United States Patent
Xie et al.

(10) Patent No.: US 8,933,106 B2
(45) Date of Patent: Jan. 13, 2015

(54) 2-(4-SUBSTITUTED PHENYLAMINO) POLYSUBSTITUTED PYRIDINE COMPOUNDS AS INHIBITORS OF NON-NUCLEOSIDE HIV REVERSE TRANSCRIPTASE, PREPARATION METHODS AND USES THEREOF

(75) Inventors: Lan Xie, Beijing (CN); Xingtao Tian, Beijing (CN); Kuo-Hsiung Lee, Chapel Hill, NC (US); Shibo Jiang, Shanghai (CN); Hong Lu, Bayside, NY (US)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 529 days.

(21) Appl. No.: 13/123,494

(22) PCT Filed: Sep. 28, 2009

(86) PCT No.: PCT/CN2009/001097
§ 371 (c)(1),
(2), (4) Date: Aug. 2, 2011

(87) PCT Pub. No.: WO2010/040275
PCT Pub. Date: Apr. 15, 2010

(65) Prior Publication Data
US 2012/0053213 A1 Mar. 1, 2012

(30) Foreign Application Priority Data
Oct. 9, 2008 (CN) .......................... 2008 1 0167051

(51) Int. Cl.
A61K 31/44 (2006.01)
C07D 213/72 (2006.01)
C07D 213/75 (2006.01)
A61K 31/4427 (2006.01)
C07D 213/74 (2006.01)

(52) U.S. Cl.
CPC ............. A61K 31/44 (2013.01); A61K 31/4427 (2013.01); C07D 213/74 (2013.01)
USPC ............ 514/352; 546/304; 546/305; 546/307

(58) Field of Classification Search
CPC . C07D 213/61; C07D 213/76; A61K 31/4418
USPC ........................... 546/304, 305, 307; 514/352
See application file for complete search history.

(56) References Cited

U.S. PATENT DOCUMENTS

| 3,853,895 | A | * | 12/1974 | Lamm et al. | 546/289 |
| 3,947,463 | A | * | 3/1976 | Fleckenstein et al. | 546/288 |
| 6,350,746 | B1 | | 2/2002 | Buckman et al. | |
| 7,125,879 | B2 | | 10/2006 | Guillemont et al. | 514/256 |
| 7,166,738 | B2 | | 1/2007 | Dunn et al. | 558/414 |

FOREIGN PATENT DOCUMENTS

| CN | 1541215 | 10/2004 |
| CN | 1946680 | 4/2007 |
| CN | 101407476 | 4/2009 |

OTHER PUBLICATIONS

International Search Report for corresponding PCT Application No. PCT/CN2009/001097, 2 pages.
Supplementary European Search Report corresponding to European Application No. EP 09 81 8739, (5 pages) dated Jun. 22, 2012.
Tian et al., "Discovery of diarylpyridine derivatives as novel non-nucleoside HIV-1 reverse transcriptase inhibitors," *Bioorganic & Medicinal Chemistry Letters* 19:5482-5485 (2009).
Wagaw et al., "The Synthesis of Aminopyridines: A Method Employing Palladium-Catalyzed Carbon-Nitrogen Bond Formation," *J. Org. Chem.* 61:7240-7241 (1996).

* cited by examiner

*Primary Examiner* — Shengjun Wang
(74) *Attorney, Agent, or Firm* — Seed IP Law Group PLLC

(57) ABSTRACT

The invention relates to 2-(4-Substituted phenylamino) polysubstituted pyridine compounds as inhibitors of non-nucleoside HIV reverse transcriptase, preparation methods and uses thereof. Specifically, the invention relates to compounds of formula I or the pharmaceutically acceptable salts thereof, wherein $R_1$, $R_2$, $R_3$, $R_4$, $R_5$, $R_6$, $R_7$ and X are as defined in the description. The compounds of formula I of the invention are a type of anti-HIV active compounds having new backbone structure.

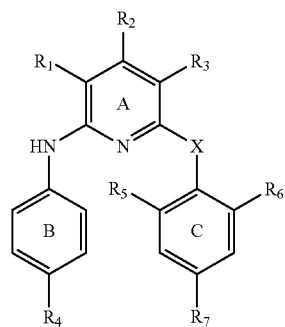

16 Claims, No Drawings

2-(4-SUBSTITUTED PHENYLAMINO) POLYSUBSTITUTED PYRIDINE COMPOUNDS AS INHIBITORS OF NON-NUCLEOSIDE HIV REVERSE TRANSCRIPTASE, PREPARATION METHODS AND USES THEREOF

TECHNICAL FIELD

The invention relates to 2-(4-substituted phenylamino) polysubstituted pyridine compounds having anti-HIV activity, their preparation methods, pharmaceutical compositions comprising the compounds and uses of the compounds for the preparation of anti-HIV drugs.

BACKGROUND ART

Human immunodeficiency virus (HIV) is a type of RNA virus. The surface of the virus is a bilayer lipid membrane. The membrane envelops therein 2 single stranded RNA and some important enzymes (such as reverse transcriptase, protease, integrase) and structural proteins (p24, p17, p7 and etc.). There are two very important glucoproteins gp120 and gp41 on the membrane surface of the virus. gp120 lies in the exterior of the membrane, and gp41 crosses over the bilayer lipid membrane and forms together with gp120 a composite. Their main function is to identify and attach the cells having CD4 surface receptor, for example, lymphocytes (T cells), macrophages and etc., in human immune system. HIV cannot reproduce in vitro, but can only replicate and regenerate by the aid of human cells. The replication process of HIV may be roughly divided into the following stages: binding and fusion of virus and host cells; reverse transcription, integration, transcription and translation of virus gene; assembly and release of virus. HIV virus is continuously replicated according to such a cycle process, to infect human immunocytes and destroy human immune system, which finally leads to the complete loss of human immune function, so that the patients are in the risk of various infections without any resisting ability. In theory, any drug, only if it blocks a link in the replication process of virus, can fulfill the purpose of inhibiting virus and treating diseases.

Until now, there are more than 30 types of chemical drugs and combinations thereof useful for resisting HIV infection and treating AIDS in clinical on the market. According to their action mechanism, the existing drugs are divided into the following five types: nucleoside reverse transcriptase inhibitors (NRTIs), non-nucleoside reverse transcriptase inhibitors (NNRTIs), protease inhibitors (PIs), fusion inhibitors (Enfuvirtide) and entry inhibitors (Maraviroc). The existing drugs used alone or in combination can effectively inhibit the replication of virus in vivo, but the main problem that all of them are confronted with is drug resistance. After acting with drug for a certain period of time, HIV virus may have some kind of variation. Variant virus can be free from the inhibition of drug, and, just like the case before medication, a large quantity of viruses continue to be replicated in vivo. Therefore, it has always been a hot spot in the field of drug research in recent years to search and develop a new generation of anti-AIDS drugs having new structure type, new action mechanism, new target site or protent inhibitory effect on drug-resistant virus.

Up to now, there are four non-nucleoside reverse transcriptase inhibitors [Nevirapine, Delavirdine, Efavirenz, Entravine] on the market. This type of drugs have various advantages including structure diversity, high efficiency, low toxicity, clear target site and action mechanism, noncompetitive inhibitors and etc., and play an important role in anti-HIV combination therapy (HAART). However, the problems associated with these drugs mainly include that the virus is easy to produce drug resistance or the drugs are taken at a relatively high frequency every day. In order to overcome the drawbacks of the existing drugs, it is necessary to search for a new generation of drugs as inhibitors of non-nucleoside reverse transcriptase, which are capable of effectively inhibiting the replication of wild type and multidrug-resistant HIV virus strains.

CONTENTS OF THE INVENTION

Summary of the Invention

The first aspect of the invention is to provide a compound of formula I:

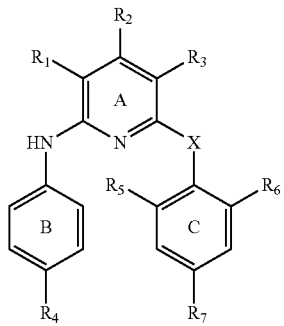

or a pharmaceutically acceptable salt thereof,
wherein,
$R_1$, $R_2$ and $R_3$ are each independently —H, halo, —$NO_2$, —$NH_2$, —NHR, —$N(R)_2$, —CN, —OH, $C_{1-6}$ alkyl, $C_{1-6}$ alkoxy, —$CF_3$, —COOH, —$SO_3H$, —$CONH_2$, —CONHR' or —COOR', or, $R_1$ and $R_2$ or $R_2$ and $R_3$ may together form —$OCH_2O$—;
$R_4$ is —CN, —CH=$CH_2$, —C≡CH, $C_{1-6}$ alkyl, $C_{1-6}$ alkoxy, —$CF_3$, halo, —$NH_2$, —OH, —COOH, —$SO_3H$, —C≡CR' or —CH=CHR';
$R_5$ and $R_6$ are each independently halo, $C_{1-6}$ alkyl, $C_{1-6}$ alkoxy, —$CF_3$, —$NH_2$, —OH, —COOH, —$SO_3H$, —COOR', —$NO_2$, —CN, —H, or $C_{1-6}$ hydrocarbyl;
$R_7$ is —CN, —HC=CH—CN, halo, $C_{1-6}$ alkyl, $C_{1-6}$ alkoxy, —$NH_2$, —$CH_2$—NHR', —OH, —$NO_2$, —$CF_3$, —CH=$CH_2$, —C≡CH, —C≡CR', —CH=CHR', —CH=CHCOR', CHO, —C≡CR'', —CH=CHR'', —C≡C—CN, $C_{1-6}$ hydrocarbyl, a five- or six-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;
R' is H or $C_{1-6}$ hydrocarbyl; R'' is $NO_2$, $NH_2$, or $N_3$;
X is selected from the group consisting of —NH—, —O—, —S—, —$CH_2$—, —CO—, —CHOH—, —CHOR—, —NR—, —NCOR—; and
R is $C_{1-4}$ hydrocarbyl.

The compounds according to any aspect of the foregoing or following context of the invention, wherein X is —O—.

The compounds according to any aspect of the foregoing or following context of the invention, wherein the compound of formula I has the following formula Ia:

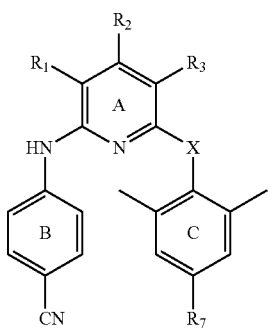

or a pharmaceutically acceptable salt thereof,
wherein,
$R_1$ and $R_3$ are each independently —$NO_2$, —$NH_2$, halo, —OH, —CN or —$N(R)_2$;
$R_2$ is —H;
$R_7$ is —CN, —HC=CH—CN, halo, —$CH_3$, —$OCH_3$, —$NH_2$, —$CH_2$—NHR', —OH, —$NO_2$, —$CF_3$, —CH=$CH_2$, —C≡CH, —C≡CR', —CH=CHR', —CH=CHCOR', —CHO, —C≡CR", —CH=CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;
R' is H or $C_{1-6}$ hydrocarbyl; R" is $NO_2$, $NH_2$, or $N_3$;
X is —O—, —NH— or —NCOR—; and
R is $C_{1-4}$ hydrocarbyl.

The compounds according to any aspect of the foregoing or following context of the invention, wherein the compound of formula I has the following formula Ia:

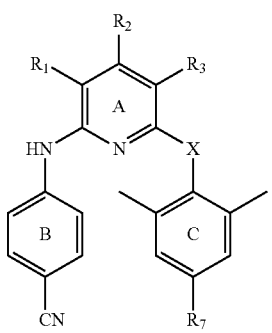

or a pharmaceutically acceptable salt thereof,
wherein,
$R_1$ is —$NO_2$, —$NH_2$, halo, —OH, —CN or —$N(R)_2$;
$R_2$ and $R_3$ are —H;
$R_7$ is —CN, —HC=CH—CN, halo, —$CH_3$, —$OCH_3$, —$NH_2$, —$CH_2$—NHR', —OH, —$NO_2$, —$CF_3$, —CH=$CH_2$, —C≡CH, —CH=CHCOR', —C≡CR', —CH=CHR', —CHO, —C≡CR", —CH=CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;
R' is H or $C_{1-6}$ hydrocarbyl; R" is $NO_2$, $NH_2$, or $N_3$;
X is —O—, —NH— or —NCOR—; and
R is $C_{1-4}$ hydrocarbyl.

The compounds according to any aspect of the foregoing or following context of the invention, wherein the compound of formula I has the following formula Ia:

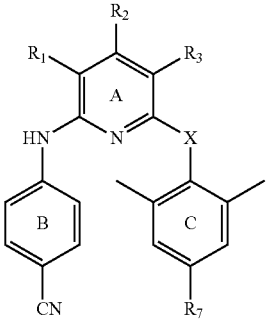

or a pharmaceutically acceptable salt thereof,
wherein,
$R_2$ is —$NO_2$, —$NH_2$, halo, —OH, —CN or —$N(R)_2$;
$R_1$ and $R_3$ are H;
$R_7$ is —CN, —HC=CH—CN, halo, —$CH_3$, —$OCH_3$, —$NH_2$, —OH, —$CH_2$—NHR', —$NO_2$, —$CF_3$, —CH=$CH_2$, —C≡CH, —C≡CR', —CH=CHR', —CH=CHCOR', —CHO, —C≡CR", —CH=CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;
R' is H or $C_{1-6}$ hydrocarbyl; R" is $NO_2$, $NH_2$, or $N_3$;
X is —O—, —NH—, —NCOR—; and
R is $C_{1-4}$ hydrocarbyl.

The compounds according to any aspect of the foregoing or following context of the invention, wherein the compound of formula I has the following formula Ia:

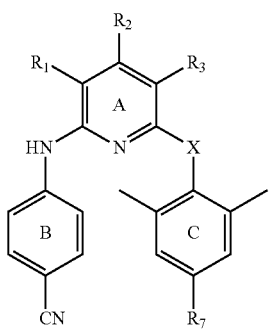

or a pharmaceutically acceptable salt thereof,
wherein,
$R_3$ is —$NO_2$, —$NH_2$, halo, —OH, —CN or —$N(R)_2$;
$R_1$ and $R_2$ are H;
$R_7$ is —CN, —HC=CH—CN, halo, —$CH_3$, —$OCH_3$, —$NH_2$, —$CH_2$—NHR', —OH, —$NO_2$, —$CF_3$, —CH=$CH_2$, —C≡CH, —C≡CR', —CH=CHR', —CH=CHCOR', —CHO, —C≡CR", —CH=CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;

R' is H or $C_{1-6}$ hydrocarbyl; R" is $NO_2$, $NH_2$, or $N_3$;

X is —O—, —NH—, —NCOR—; and

R is $C_{1-4}$ hydrocarbyl.

The compounds according to any aspect of the foregoing or following context of the invention, wherein the compound of formula I has the following formula Ia:

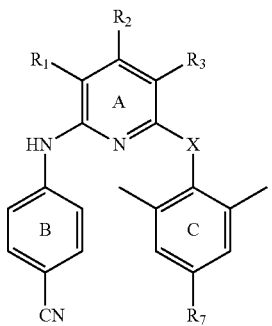

Ia or a pharmaceutically acceptable salt thereof, wherein, $R_1$, $R_2$ and $R_3$ are —H;

$R_7$ is —CN, —HC═CH—CN, halo, —$CH_3$, —$OCH_3$, —$NH_2$, —$CH_2$—NHR', —OH, —$NO_2$, —$CF_3$, —CH═$CH_2$, —C≡CH, —C≡CR', —CH═CHR', —CH═CHCOR', —CHO, —C≡CR", —CH═CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;

R' is H or $C_{1-6}$ hydrocarbyl; R" is $NO_2$, $NH_2$, or $N_3$;

X is —O—, —NH— or —NCOR—; and

R is $C_{1-4}$ hydrocarbyl.

The compounds according to any aspect of the foregoing or following context of the invention, wherein the compound of formula I has the following formula Ia:

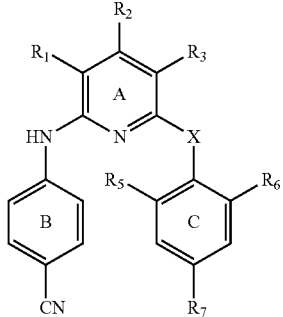

Ia or a pharmaceutically acceptable salt thereof, wherein, $R_1$ is —$NO_2$, or —$NH_2$;

$R_2$ and $R_3$ are —H;

$R_5$ and $R_6$ are each independently halo, $C_{1-6}$ alkyl, $C_{1-6}$ alkoxy, —$CF_3$, —$NH_2$, —OH, —COOH, —$NO_2$, —CN, or —H; preferably, $R_5$ and $R_6$ are each independently halo, $C_{1-4}$ alkyl, —$NH_2$, —OH, —$NO_2$, or —CN;

$R_7$ is —CN, —HC═CH—CN, halo, —$CH_3$, —$OCH_3$, —$NH_2$, —$CH_2$—NHR', —OH, —$NO_2$, —$CF_3$, —CH═$CH_2$, —C≡CH, —C≡CR', —CH═CHR', —CH═CHCOR', —CHO, —C≡CR", —CH═CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;

R' is H, $C_{1-6}$ alkyl, $C_{2-6}$ alkenyl, $C_{2-6}$ alkynyl, $C_{3-6}$ cycloalkyl; R" is $NO_2$, $NH_2$, or $N_3$;

X is —O—, —NH— or —NCOR—; and

R is $C_{1-4}$ hydrocarbyl.

The compounds according to any aspect of the foregoing or following context of the invention, which are selected from the group consisting of:

2-(4-cyanophenylamino)-6-(2,6-dimethyl-4-bromophenoxy)-3-nitropyridine;

2-(4-cyanophenylamino)-6-(2,6-dimethyl-4-cyanophenoxy)-3-nitropyridine;

2-(4-cyanophenylamino)-6-(2,4,6-trimethylphenoxy)-3-nitropyridine;

2-(4-cyanophenylamino)-6-(2,6-dimethyl-4-formylphenoxy)-3-nitropyridine;

2-(4-cyanophenylamino)-6-(2,6-dimethyl-4-cyanovinyl phenoxy)-3-nitropyridine;

3-amino-2-(4-cyanophenylamino)-6-(2,6-dimethyl-4-cyanophenoxy)-pyridine;

3-amino-2-(4-cyanophenylamino)-6-(2,6-dimethyl-4-hydroxymethylphenoxy)-pyridine;

2-(4-cyanophenylamino)-6-(2,6-dimethyl-4-hydroxymethylphenoxy)-3-nitropyridine;

2-(4-cyanophenylamino)-6-(2,6-dimethyl-4-allylphenoxy)-3-nitropyridine;

3-amino-2-(4-cyanophenylamino)-6-(2,6-dimethyl-4-cyanovinylphenoxy)-pyridine;

2-(4-cyanophenylamino)-6-(2,6-dimethyl-4-methylphenylamino)-3-nitropyridine;

3-amino-2-(4-cyanophenylamino)-6-(2,6-dimethyl-4-bromophenoxy)-pyridine;

3-amino-2-(4-cyanophenylamino)-6-(2,6-dimethyl-4-allylphenoxy)-pyridine;

2-(4-cyanophenylamino)-6-(2,6-dimethyl-4-(1-hydroxy-2-nitroethyl)phenoxy)-3-nitropyridine;

2-(4-cyanophenylamino)-6-(2,6-dimethyl-4-(2-cyclopropylaminomethyl)phenoxy)-3-nitropyridine;

2-(4-cyanophenylamino)-6-(2,6-dimethyl-4-iodophenoxy)-3-nitropyridine;

2-(4-cyanophenylamino)-6-(2,6-dimethyl-4-nitrophenoxy)-3-nitropyridine;

2-(4-cyanophenylamino)-6-(2,6-dimethyl-4-(3-methyl-3-hydroxy-1-butynyl)phenoxy)-3-nitropyridine;

3-amino-2-(4-cyanophenylamino)-6-(2,6-dimethyl-4-(3-methyl-3-hydroxy-1-butynyl)ethynylphenoxy)-pyridine;

2-(4-cyanophenylamino)-6-(2,6-dimethyl-4-(cyclopropylethynyl)phenoxy)-3-nitropyridine;

3-amino-2-(4-cyanophenylamino)-6-(2,6-dimethyl-4-(cyclopropylethynyl)phenoxy)-pyridine;

2-(4-cyanophenylamino)-6-(2,6-dimethyl-4-ethynylphenoxy)-3-nitropyridine;

3-amino-2-(4-cyanophenylamino)-6-(2,6-dimethyl-4-ethynylphenoxy)-pyridine;

3-amino-2-(4-cyanophenylamino)-6-(2,6-dimethyl-4-aminophenoxy)-pyridine;

3-amino-2-(4-cyanophenylamino)-6-(2,6-dimethyl-4-iodophenoxy)-pyridine;

2-(4-cyanophenylamino)-6-(2,4,6-tribromophenoxy)-3-nitropyridine;
2-(4-cyanophenylamino)-6-(2,6-dibromo-4-formylphenoxy)-3-nitropyridine;
2-(4-cyanophenylamino)-6-(2,6-dibromo-4-hydroxymethylphenoxy)-3-nitropyridine;
2-(4-cyanophenylamino)-6-(2,6-difluorophenoxy)-3-nitropyridine; and
2-(4-cyanophenylamino)-6-(2,6-dibromo-4-cyanovinylphenoxy)-3-nitropyridine,
or a pharmaceutically acceptable salt thereof.

The second aspect of the invention is to provide a method for preparing the compound according to any item of the first aspect of the invention, the reaction route being shown as follows:

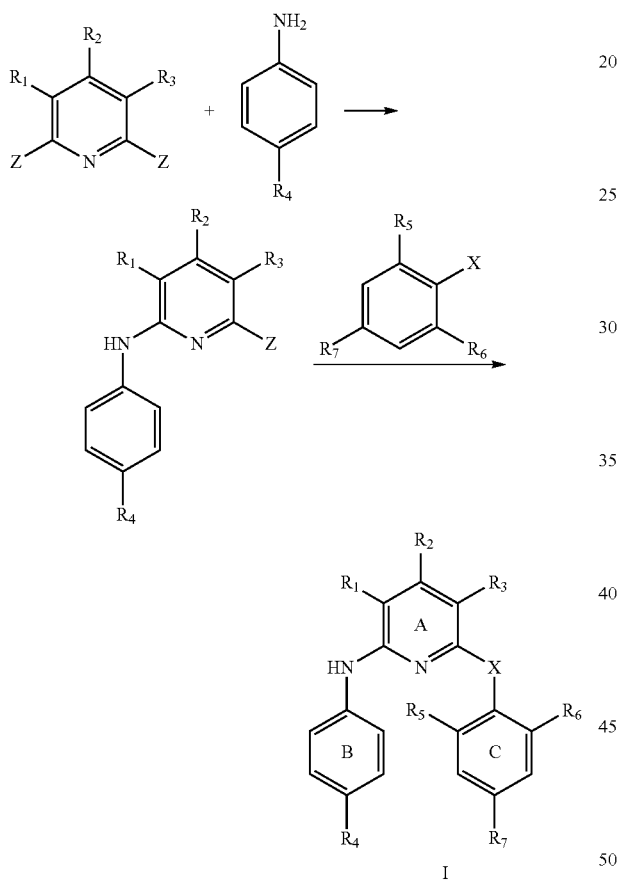

Z = Cl, Br, I
X = NH$_2$, OH, NR', SH
X = NH, O, NR', S wherein R$_1$, R$_2$, R$_3$, R$_4$, R$_5$, R$_6$, R$_7$, and X are the same as defined above for the compound of formula I. The method comprises reacting a substituted 2,6-dihalopyridine compound of formula II with a para-substituted phenylamine compound under the action of a base, or reacting in the absence of solvent, to form a 2-(4-substituted phenylamino) polysubstituted pyridine compound of formula IV; thereafter, coupling the intermediate of formula IV with a polysubstituted phenol or phenylamine compound, or heating in the presence of palladium catalysts or coupling under microwave condition, to form a 2-(4-substituted phenylamino) polysubstituted pyridine compound of formula I.

The third aspect of the invention is to provide a pharmaceutical composition, which comprises the compound according to any item of the first aspect of the invention or a pharmaceutically acceptable salt thereof and one or more pharmaceutically acceptable carriers or excipients.

The fourth aspect of the invention is to provide use of the compound according to any item of the first aspect of the invention or a pharmaceutically acceptable salt thereof for the manufacture of a medicament for the treatment of diseases or conditions associated with HIV infection.

The fifth aspect of the invention is to provide a method of treating diseases or conditions associated with HIV infection comprising administering to a subject in need thereof a therapeutically effective amount of the compound according to any item of the first aspect of the invention or a pharmaceutically acceptable salt thereof.

DETAILED DESCRIPTION OF THE INVENTION

All the documents as mentioned in the invention are incorporated herein in their entireties by citation, and, if these documents denote different meanings from the contents as described in the invention, it is the contents as described in the invention that are adopted. In addition, various terms and phrases used in the invention have their general meanings as well known to a person skilled in the art, even so, more detailed illustrations and explanations about these terms and phrases are still given in the invention, if the terms and phrases as mentioned denote different from their general meanings, it is the meanings as given in the invention that are adopted.

During the study of new anti-HIV drugs, the inventors found that a class of compound having new structure exhibited a quite potent anti-HIV activity.

The invention is further described in detail below. The first aspect of the invention relates to a compound of formula I having a 2-(4-substituted phenylamino) polysubstituted pyridine backbone structure as shown in formula I:

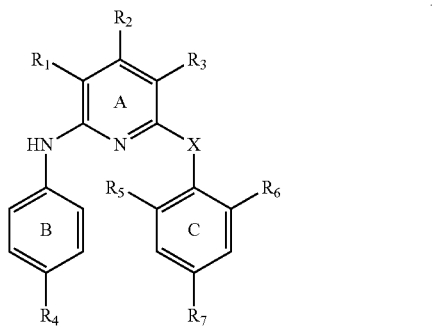

or a pharmaceutically acceptable salt thereof,
wherein,
R$_1$, R$_2$ and R$_3$ are each independently —H, halo, —NO$_2$, —NH$_2$, —NHR, —N(R)$_2$, —CN, —OH, C$_{1-6}$ alkyl, C$_{1-6}$ alkoxy, —CF$_3$, —COOH, —SO$_3$H, —CONH$_2$, —CONHR' or —COOR',
or, R$_1$ and R$_2$ or R$_2$ and R$_3$ may together form —OCH$_2$O—;
R$_4$ is —CN, —CH=CH$_2$, —C≡CH, C$_{1-6}$ alkyl, C$_{1-6}$ alkoxy, —CF$_3$, halo, —NH$_2$, —OH, —COOH, —SO$_3$H, —C≡CR' or —CH=CHR';
R$_5$ and R$_6$ are each independently halo, C$_{1-6}$ alkyl, C$_{1-6}$ alkoxy, —CF$_3$, —NH$_2$, —OH, —COOH, —SO$_3$H or —COOR', —NO$_2$, —CN, —H, or C$_{1-6}$ hydrocarbyl;

$R_2$ is —CN, —HC═CH—CN, halo, —CH$_3$, —OCH$_3$, —NH$_2$, —CH$_2$—NHR', —OH, —NO$_2$, —CF$_3$, —CH═CH$_2$, —C≡CH, —C≡CR', —CH═CHR', —CH═CHCOR', —CHO, —C≡CR", —CH═CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;

R' is H or C$_{1-6}$ hydrocarbyl or cyclohydrocarbyl; R" is NO$_2$, NH$_2$, or N$_3$;

X is selected from the group consisting of —NH—, —O—, —S—, —CH$_2$—, —CO—, —CHOH—, —CHOR—, —NR—, —NCOR—; and R is C$_{1-4}$ hydrocarbyl.

The second aspect of the invention relates to a method for preparing a compound of formula I or a pharmaceutically acceptable salt thereof.

The third aspect of the invention relates to a pharmaceutical composition comprising at least one compound of formula I or a pharmaceutically acceptable salt thereof and one or more pharmaceutically acceptable carriers or excipients.

The fourth aspect of the invention relates to use of the compound of formula I or a pharmaceutically acceptable salt thereof for the manufacture of a medicament for the treatment of diseases or conditions associated with HIV infection.

For nomenclature of the compound of formula I in the invention, the ring atoms in the rings A, B and C, especially in the rings A and C, may be numbered according to the following exemplary order:

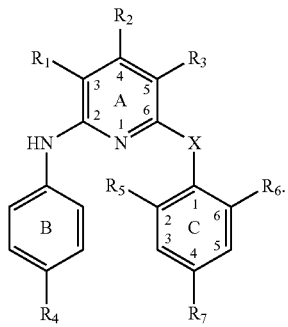

The terms "halo", "halogen", "Hal" or "halogenated" used herein refer to fluorine, chloloine, bromine and iodine.

The term "hydrocarbyl" used herein includes alkyl (for example, linear alkyl, branched alkyl), cycloalkyl, alkenyl and alkynyl. In one embodiment, the term "C$_{1-6}$ hydrocarbyl" used includes C$_{1-6}$ alkyl, C$_{2-6}$ alkenyl, C$_{2-6}$ alkynyl, C$_{3-6}$ cycloalkyl, C$_{3-6}$cycloalkenyl. In one embodiment, the term "C$_{1-6}$ hydrocarbyl" used includes "C$_{1-4}$ hydrocarbyl". In one embodiment, the term "C$_{1-4}$ hydrocarbyl" used includes C$_{1-4}$ alkyl, C$_{2-4}$ alkenyl, C$_{2-4}$ alkynyl, C$_{3-4}$ cycloalkyl, C$_{3-4}$cycloalkenyl. In one embodiment, the term "C$_{1-6}$ hydrocarbyl" includes methyl, ethyl, propyl, isopropyl, n-butyl, isobutyl, t-butyl, pentyl, neopentyl, hexyl, ethenyl, propenyl, allyl, butenyl, ethynyl, propargyl, cyclopropyl, cyclobutyl, cyclopentyl, cyclohexyl, cyclobutenyl.

The term "five-membered heteroaryl" used herein refers to a five-membered aromatic ring system containing 1-3 heteratoms selected from O, S or N, which includes, but is not limited to, furyl, pyrrolyl, thienyl, pyrazolyl, and etc.

The term "five-membered heteroaryl which is substituted on its ring with carbonyl (either aldehyde or ketone group), cyano, α,β-unsaturated cyano, alkenyl, alkynyl, aldehyde or ketone" used herein includes, but is not limited to:

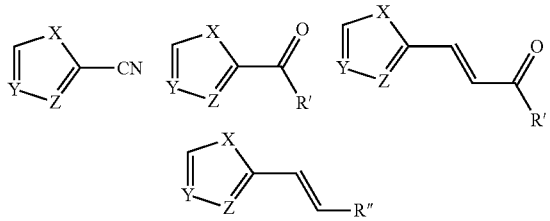

wherein,
R' may be H, C$_{1-6}$ hydrocarbyl;
R" may be H, —CN, NO$_2$, N$_3$, C$_{1-4}$ hydrocarbyl;
X, Y, Z are each independently a heteroatom selected from N, O, S or a carbon atom.

According to one embodiment of the invention, the invention relates to a compound of formula I shown as follows:

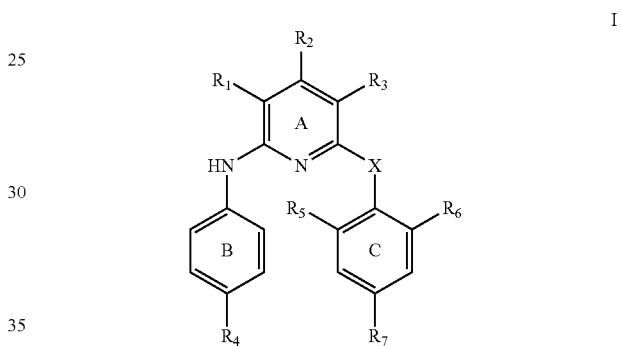

or a pharmaceutically acceptable salt thereof,
wherein, $R_1$, $R_2$ and $R_3$ are each independently —H, halo, —NO$_2$, —NH$_2$, —NHR, —N(R)$_2$, —CN, —OH, C$_{1-6}$ alkyl, C$_{1-6}$ alkoxy, —CF$_3$, —COOH, —SO$_3$H, —CONH$_2$, —CONHR' or —COOR', or, $R_1$ and $R_2$ or $R_2$ and $R_3$ may together form —OCH$_2$O—;

$R_4$ is —CN, —CH═CH$_2$, —C≡CH, C$_{1-6}$ alkyl, C$_{1-6}$ alkoxy, —CF$_3$, halo, —NH$_2$, —OH, —COOH, —SO$_3$H, —C≡CR' or —CH═CHR';

$R_5$ and $R_6$ are each independently halo, C$_{1-6}$ alkyl, C$_{1-6}$ alkoxy, —CF$_3$, —NH$_2$, —OH, —COOH, —SO$_3$H, —COOR', —NO$_2$, —CN, —H, or C$_{1-6}$ hydrocarbyl;

$R_7$ is —CN, —HC═CH—CN, halo, C$_{1-6}$ alkyl, C$_{1-6}$ alkoxy, —NH$_2$, —CH$_2$—NHR', —OH, —NO$_2$, —CF$_3$, —CH═CH$_2$, —C≡CH, —C≡CR', —CH═CHR', —CH═CHCOR', —CHO, —C≡CR", —CH═CHR", —C≡C—CN, C$_{1-6}$ hydrocarbyl, a five- or six-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;

R' is H or C$_{1-6}$ hydrocarbyl such as C$_{1-4}$ chain hydrocarbyl or C$_{3-6}$ hydrocarbyl cyclohydrocarbyl; R" is NO$_2$, NH$_2$, or N$_3$;

X is selected from the group consisting of —NH—, —O—, —S—, —CH$_2$—, —CO—, —CHOH—, —CHOR—, —NR—, —NCOR—; and R is C$_{1-4}$ hydrocarbyl.

According to one preferred embodiment of the invention, X is —O—.

According to one preferred embodiment of the invention, the compound of formula I in the invention has the following formula Ia:

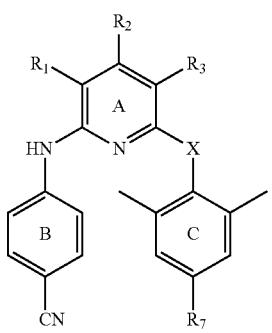

or a pharmaceutically acceptable salt thereof,
wherein,
$R_1$ and $R_3$ are each independently —$NO_2$, —$NH_2$, halo, —OH, —CN or —$N(R)_2$;
$R_2$ is —H;
$R_7$ is —CN, —HC=CH—CN, halo, —$CH_3$, —$OCH_3$, —$NH_2$, —$CH_2$—NHR', —OH, —$NO_2$, —$CF_3$, —CH=$CH_2$, —C≡CH, —C≡CR', —CH=CHR', —CH=CHCOR', —CHO, —C≡CR", —CH=CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;
R' is H or $C_{1-6}$ hydrocarbyl; R" is $NO_2$, $NH_2$, or $N_3$;
X is —O—, —NH— or —NCOR—; and
R is $C_{1-4}$ hydrocarbyl.

According to another preferred embodiment of the invention, the compound of formula I has the above formula Ia, wherein
$R_1$ is —$NO_2$, —$NH_2$, halo, —OH, —CN or —$N(R)_2$;
$R_2$ and $R_3$ are —H;
$R_7$ is —CN, —HC=CH—CN, halo, —$CH_3$, —$OCH_3$, —$NH_2$, —$CH_2$—NHR', —OH, —$NO_2$, —$CF_3$, —CH=$CH_2$, —C≡CH, —CH=CHCOR', —C≡CR', —CH=CHR', —CHO, —C≡CR", —CH=CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;
R' is H or $C_{1-6}$ hydrocarbyl; R" is $NO_2$, $NH_2$, or $N_3$;
X is —O—, —NH— or —NCOR—; and
R is $C_{1-4}$ hydrocarbyl.

According to still another preferred embodiment of the invention, the compound of formula I has the above formula Ia, wherein
$R_2$ is —$NO_2$, —$NH_2$, halo, —OH, —CN or —$N(R)_2$;
$R_1$ and $R_3$ are H;
$R_7$ is —CN, —HC=CH—CN, halo, —$CH_3$, —$OCH_3$, —$NH_2$, —OH, —$CH_2$—NHR', —$NO_2$, —$CF_3$, —CH=$CH_2$, —C≡CH, —C≡CR', —CH=CHR', —CH=CHCOR', —CHO, —C≡CR", —CH=CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;
R' is H or $C_{1-6}$ hydrocarbyl; R" is $NO_2$, $NH_2$, or $N_3$;
X is —O—, —NH—, —NCOR—; and
R is $C_{1-4}$ hydrocarbyl.

According to still another preferred embodiment of the invention, the compound of formula I has the above formula Ia, wherein
$R_3$ is —$NO_2$, —$NH_2$, halo, —OH, —CN or —$N(R)_2$;
$R_1$ and $R_2$ are H;
$R_7$ is —CN, —HC=CH—CN, halo, —$CH_3$, —$OCH_3$, —$NH_2$, —$CH_2$—NHR', —OH, —$NO_2$, —$CF_3$, —CH=$CH_2$, —C≡CH, —C≡CR', —CH=CHR', —CH=CHCOR', —CHO, —C≡CR", —CH=CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;
R' is H or $C_{1-6}$ hydrocarbyl; R" is $NO_2$, $NH_2$, or $N_3$;
X is —O—, —NH—, —NCOR—; and
R is $C_{1-4}$ hydrocarbyl.

According to still another preferred embodiment of the invention, the compound of formula I has the above formula Ia, wherein
$R_3$ is —$NO_2$, —$NH_2$, halo, —OH, —CN or —$N(R)_2$;
$R_1$ and $R_2$ are H;
$R_7$ is —CN, —HC=CH—CN, halo, —$CH_3$, —$OCH_3$, —$NH_2$, —$CH_2$—NHR', —OH, —$NO_2$, —$CF_3$, —CH=$CH_2$, —C≡CH, —C≡CR', —CH=CHR', —CH=CHCOR', —CHO, —C≡CR", —CH=CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;
R' is H or $C_{1-6}$ hydrocarbyl; R" is $NO_2$, $NH_2$, or $N_3$;
X is —O— or —NH—; and
R is $C_{1-4}$ hydrocarbyl.

According to still another preferred embodiment of the invention, the compound of formula I has the above formula Ia, wherein
$R_1$ and $R_2$ or $R_2$ and $R_3$ together form —$OCH_2O$—, the remaining $R_3$ or $R_1$ being —H, OH, —$NH_2$, —$NO_2$ or halogen;
$R_7$ is —CN, —HC=CH—CN, halo, —$CH_3$, —$OCH_3$, —$NH_2$, —$CH_2$—NHR', —OH, —$NO_2$, —$CF_3$, —CH=$CH_2$, —C≡CH, —C≡CR', —CH=CHR', —CH=CHCOR', —CHO, —C≡CR", —CH=CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;
R' is H or $C_{1-6}$ hydrocarbyl; R" is $NO_2$, $NH_2$, or $N_3$;
X is —O—, —S—, —$CH_2$—, —NH—, —NCOR—; and
R is $C_{1-4}$ hydrocarbyl.

The compound of formula I according to any aspect of the foregoing or following context of the invention, wherein $R_1$, $R_2$ and $R_3$ are each independently —H, halo, —$NO_2$, —$NH_2$, or —NHR. In one embodiment, $R_1$, $R_2$ and $R_3$ are each independently —H, halo, —$NO_2$, —$NH_2$. In one embodiment, $R_1$ is —H, —$NO_2$, or —$NH_2$. In one embodiment, $R_1$ is —$NO_2$, or —$NH_2$. Wherein, R is $C_{1-4}$ hydrocarbyl; R' is H or $C_{1-6}$ hydrocarbyl; R" is $NO_2$, $NH_2$, or $N_3$.

The compound of formula I according to any aspect of the foregoing or following context of the invention, wherein $R_4$ is —CN, —CH=CH$_2$, —C≡CH, $C_{1-6}$ alkyl, $C_{1-6}$ alkoxy, —CF$_3$, halo, —NH$_2$, —OH, —COOH, —SO$_3$H, —C≡CR' or —CH=CHR'. In one embodiment, $R_4$ is —CN, $C_{1-6}$ alkyl, $C_{1-6}$ alkoxy, —CF$_3$, halo, —NH$_2$, —OH, or —COOH. In one embodiment, $R_4$ is —CN, $C_{1-6}$ alkyl, —CF$_3$, halo, —NH$_2$, or —OH. In one embodiment, $R_4$ is —CN, $C_{1-6}$ alkyl, halo, —NH$_2$. Wherein, R is $C_{1-4}$ hydrocarbyl; R' is H or $C_{1-6}$ hydrocarbyl; R" is NO$_2$, NH$_2$, or N$_3$.

The compound of formula I according to any aspect of the foregoing or following context of the invention, wherein $R_5$ and $R_6$ are each independently halo, $C_{1-6}$ alkyl, $C_{1-6}$ alkoxy, —CF$_3$, —NH$_2$, —OH, —COOH, —SO$_3$H, —COOR', —NO$_2$, —CN, —H, or $C_{1-6}$ hydrocarbyl. In one embodiment, $R_5$ and $R_6$ are each independently halo, $C_{1-6}$ alkyl, —NH$_2$, —OH, —COOH, —NO$_2$, —CN, or —H. In one embodiment, $R_5$ and $R_6$ are each independently halo, $C_{1-6}$ alkyl, —NH$_2$, —NO$_2$, —CN, or —H. In one embodiment, $R_5$ and $R_6$ are each independently fluoro, chloro, bromo, iodo, methyl, ethyl, propyl, isopropyl, butyl, or t-butyl. Wherein, R is $C_{1-4}$ hydrocarbyl; R' is H or $C_{1-6}$ hydrocarbyl; R" is NO$_2$, NH$_2$, or N$_3$.

The compound of formula I according to any aspect of the foregoing or following context of the invention, wherein $R_7$ is selected from —CN, —HC=CH—CN, halo, $C_{1-6}$ alkyl, $C_{1-6}$ alkoxy, —NH$_2$, —CH$_2$—NHR', —OH, —NO$_2$, —CF$_3$, —CH=CH$_2$, —C≡CH, —C≡CR', —CH=CHR', —CH=CHCOR', CHO, —C≡CR", —CH=CHR", —C≡C—CN, $C_{1-6}$ hydrocarbyl, a five- or six-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde or ketone. In one embodiment, $R_7$ is selected from —CN, —HC=CH—CN, halo, $C_{1-6}$ alkyl, $C_{1-6}$ alkoxy, —NH$_2$, —CH$_2$—NHR', —OH, —NO$_2$, —CF$_3$, —CH=CH$_2$, —C≡CH, —C≡CR', —CH=CHR', —CH=CHCOR', CHO, —C≡CR", —CH=CHR", —C≡C—CN, $C_{3-6}$ cycloalkyl, $C_{2-6}$ alkenyl, $C_{2-6}$ alkynyl. In one embodiment, $R_7$ is selected from —CN, —HC=CH—CN, halo, $C_{1-6}$ alkyl, $C_{1-6}$ alkoxy, —NH$_2$, —CH$_2$—NHR', —OH, —NO$_2$, —CF$_3$, —CH=CH$_2$, —C≡CH, —C≡CR', —CH=CHR', —CH=CHCOR', CHO, —C≡CR", —CH=CHR", —C≡C—CN, $C_{3-6}$ cycloalkyl, $C_{2-6}$ alkenyl, $C_{2-6}$ alkynyl. Wherein, R is $C_{1-4}$ hydrocarbyl; R' is H or $C_{1-6}$ hydrocarbyl; R" is NO$_2$, NH$_2$, or N$_3$.

The compound of formula I according to any aspect of the foregoing or following context of the invention, wherein X is selected from the group consisting of —NH—, —O—, —S—, —CH$_2$—, —CO—, —CHOH—, —CHOR—, —NR—, —NCOR—. In one embodiment, X is selected from the group consisting of —NH—, —O—, —S—, —CH$_2$—, —CO—, —NR—, —NCOR—. In one embodiment, X is selected from the group consisting of —NH—, —O—, —S—, —CH$_2$—, —CO—, —NR—. In one embodiment, X is selected from the group consisting of —NH—, —O—, —CH$_2$—, —NR—. In one embodiment, X is selected from the group consisting of —NH—, —O—. Wherein, R is $C_{1-4}$ hydrocarbyl; R' is H or $C_{1-6}$ hydrocarbyl; R" is NO$_2$, NH$_2$, or N$_3$.

The compound of formula I according to any aspect of the foregoing or following context of the invention, wherein R is $C_{1-4}$ hydrocarbyl. In one embodiment, R is selected from $C_{1-4}$ alkyl, $C_{2-4}$ alkenyl, $C_{2-4}$ alkynyl, $C_{3-4}$ cycloalkyl. In one embodiment, R is selected from methyl, ethyl, propyl, isopropyl, butyl, isobutyl, t-butyl, ethenyl, propenyl, allyl, ethynyl, propargyl, cycloalkyl, cyclobutyl.

The compound of formula I according to any aspect of the foregoing or following context of the invention, which is a compound selected from the examples of the invention, or a pharmaceutically acceptable salt thereof.

The 2-(4-substituted phenylamino) polysubstituted pyridine compounds of formula I in the invention exhibit protent anti-HIV activity and high selectivity in cell experiments (MT-2 and H9 lymphocytes) of inhibiting HIV replication. Thus, new anti-HIV drugs have prospects to be developed via a deep study to the compounds of the invention.

The compound of the invention may be prepared according to the following reaction route:

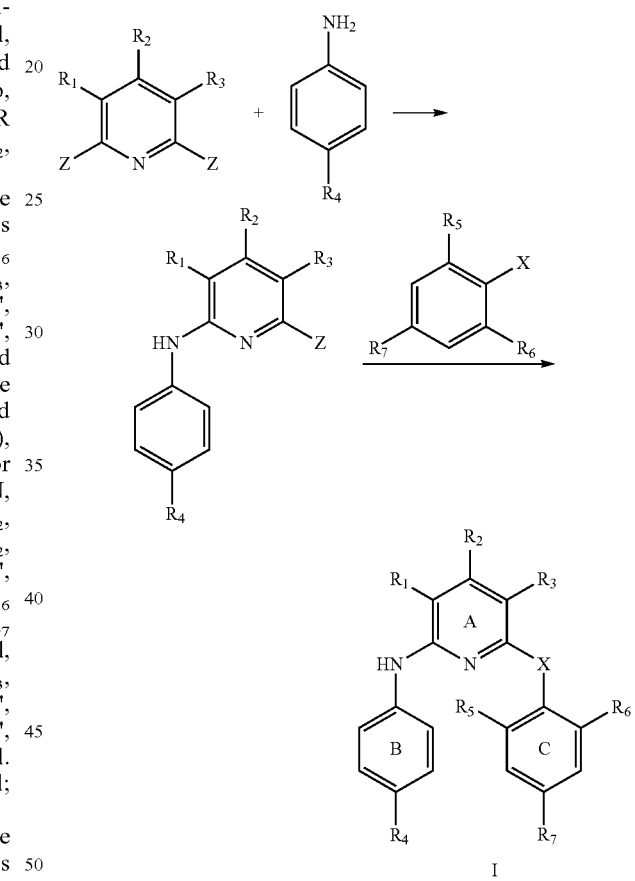

wherein $R_1$, $R_2$, $R_3$, $R_4$, $R_5$, $R_6$, $R_7$, and X are the same as defined above for the compound of formula I.

A substituted 2,6-dihalopyridine compound of formula II is reacted with a para-substituted phenylamine compound, to form a 2-(4-substituted phenylamino) polysubstituted pyridine compound, i.e., an intermediate of formula IV; thereafter, the intermediate of formula IV is coupled with a polysubstituted phenol or phenylamine compound, or heating in the presence of palladium catalysts or coupling under microwave condition, to form a 2-(4-substituted phenylamino) polysubstituted pyridine compound of formula I, i.e., the target compound.

In addition, a part of target compounds of formula I can also be formed by simultaneously carrying out the two-step coupling reactions under microwave reaction condition, i.e., "one-pot reaction".

For example, the compound of formula Ia in the invention may be prepared according to the following reaction route:

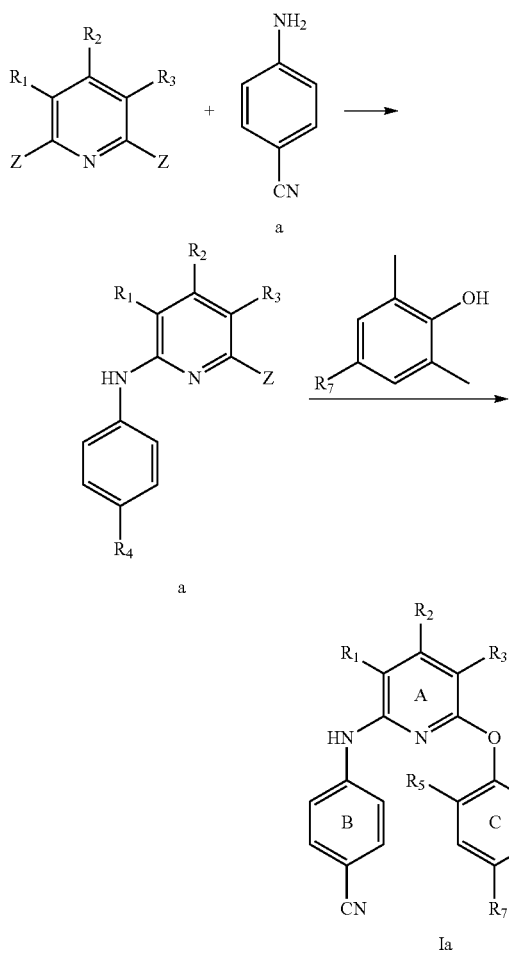

wherein, Z=halo, $R_1$, $R_2$, $R_3$, $R_4$, $R_5$, $R_6$, $R_7$ are the same as defined above for the compound of formula I, the compound of formula II having appropriate $R_1$, $R_2$ and $R_3$ substituents may be selected as the raw material according to the requirement.

Synthesis of the Intermediate of Formula IV

In concrete, in the presence of potassium t-butoxide, sodium hydride, triethylamine, pyridine, N,N-dimethylaminopyridine, sodium bicarbonate, potassium carbonate, or potassium carbonate/cuprous halide, 2,6-dihalo substituted pyridine (II) is reacted with para-substituted aniline or phenol in a solvent such as, but not limited to, ethanol, t-butanol, DMF, acetonitrile, THF or DMSO, at room temperature to below 130° C., for 5 min to 24 h, to form 2-(4-substituted phenylamino) polysubstituted pyridine or 2-(4-substituted phenoxy)polysubstituted pyridine (IVa). The charge molar ratio of the reactants II/III may be 1:1 to 1:2.

The reaction can also be carried out under microwave condition, in a solvent DMF or DMSO, at a temperature ranging from 110 to 180° C., for 5-30 min to form the intermediate of formula IVa. The base and the charge ratio of the reactants may be the same as described above.

The reaction can also be carried out in the absence of solvent under the protection of an inert gas at a temperature ranging from 50 to 180° C. The charge ratio of the reactants II/III may be the same as described above.

Synthesis of the Target Compound of Formula I

For example, when X in the formula is —O—, the compound of formula I may be synthesized according to the following methods:

Method 1: 2-(4-Substituted phenylamino)-6-halo polysubstituted pyridine (formula IVa) is reacted with polysubstituted phenol (formula V) in a solvent such as DMSO, DMF and etc., in the presence of $K_2CO_3$ as the base and Cu or cuproine (such as CuI, CuBr) as the catalyst, under the protection of nitrogen by heating to a temperature such as 100-150° C. for, for example, 2-8 h. Or, the reaction is carried out in the absence of catalyst at a temperature such as 130-150° C. for, for example, 2-24 h.

Method 2: In dried ethyl ether, a trisubstituted phenol of formula V is reacted with NaH or potassium t-butoxide to form Na salt or K salt, and then the salt and the intermediate of formula IVa are refluxed in DMF for 0.5-8 h.

Method 3: The intermediate of formula IVa is reacted with sodium or potassium phenate in DMF under microwave condition for, for example, 5-30 min.

Method 4: The intermediate of formula IVa is reacted with a substituted phenol (formula V) and potassium carbonate in DMSO under microwave condition for, for example, 5-30 min.

For another example, when X in the formula is —NH—, the compound of formula I may be synthesized according to the following methods:

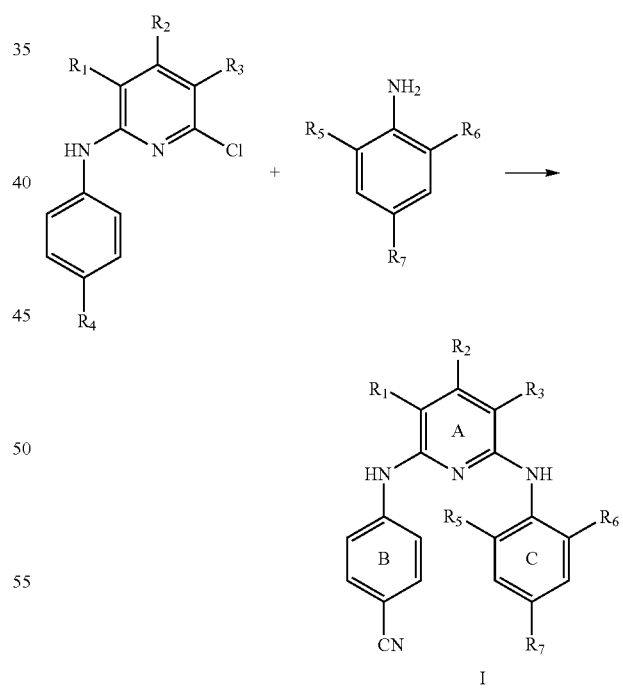

wherein the various substituents are the same as defined above for the compound of formula I, the compound of formula IV having appropriate $R_1$, $R_2$ and $R_3$ substituents may be selected as the raw material according to the requirement.

Method 5: The intermediate-substituted pyridine (formula IV) and substituted phenylamine (formula V) are reacted in an aprotic polar solvent (such as DMSO or DMF), in the presence of cuproine such as Cu, CuI or CuBr as the catalyst and $K_2CO_3$ as the base, under the protection of nitrogen at a temperature such as 140-160° C. for, for example, 2-24 h.

Method 6: The intermediate-substituted pyridine (formula IV) and substituted phenylamine (formula V) are reacted in the presence of a palladium reagent as the catalyst, toluene as the solvent and cesium carbonate as the base, under the protection of nitrogen at a temperature such as about 100° C. for, for example, 1-24 h.

Method 7: If arylamine (formula VI) is liquid, other solvent may not be needed, and the arylamine of formula VI and the intermediate of formula IV may be directly mixed and reacted at the boiling temperature of the arylamine under microwave condition for, for example, 15-20 min.

Method 8: Arylamine (formula V) and the intermediate-substituted pyridine (formula IV) in a molar ratio of 4:1 are reacted in a solvent such as DMSO or NMP in the presence of potassium t-butoxide under microwave condition at a temperature such as 200-250° C. for, for example, 15-30 min.

Likewise, the compound of formula I wherein X is otherwise defined can be prepared. For example, by reference to the above methods for the preparation of the compound of formula I wherein X is —NH—, a person skilled in the art, in accordance with the knowledge he or she grasps and the method as well known in the art, can obtain the compounds of formula I wherein X is —NR— and —NCOR—, wherein R is $C_{1-4}$ hydrocarbyl such as methyl, ethyl, propyl, and etc.

In the methods for the synthesis of the compound of formula I in the invention, various raw materials used in the reaction can be obtained by a person skilled in the art according to the existing knowledge, or can be prepared according to the well-known methods as disclosed in documents, or are commercially available. As for the intermediates, raw materials, reagents, reaction conditions and etc. used in the above reaction schemes, all of them can be appropriately altered by a person skilled in the art according to the existing knowledge. Or, a person skilled in the art can also synthesize other compounds of formula I that are not specifically enumerated in the invention according to the method as described in the second aspect of the invention.

The compound of the invention can be used either in itself or in the form of its pharmaceutically acceptable salt. The pharmaceutically acceptable salts of the compound of formula I include conventional salts formed with pharmaceutically acceptable inorganic acid or organic acid, or inorganic base or organic base. Suitable examples of acid addition salts include salts formed with hydrochloric acid, hydrobromic acid, sulfuric acid, phosphoric acid, nitric acid, perchloric acid, fumaric acid, acetic acid, propionic acid, succinic acid, glycolic acid, formic acid, lactic acid, maleic acid, tartaric acid, citric acid, pamoic acid, malonic acid, hydroxymaleic acid, phenylacetic acid, glutamic acid, benzoic acid, salicylic acid, toluenesulfonic acid, methanesulfonic acid, naphthalene-2-sulfonic acid, benzenesulfonic acid, naphtholcarboxylic acid, hydriodic acid, malic acid, tannic acid and etc. Suitable examples of base addition salts include salts formed with sodium, lithium, potassium, magnesium, aluminum, calcium, zinc, N,N'-dibenzylethylenediamine, chloroprocaine, choline, diethanolamine, ethylenediamine, N-methylglucosamine, procaine and etc. When the compound of the invention is related herein, it includes the compound of formula I and a pharmaceutically acceptable salt thereof.

The compound of formula I or a pharmaceutically acceptable salt thereof in the invention further includes its isomers, racemates, enantiomers, diastereomers, enantiomer enriched products, solvates, and esters. The compound of formula I of the invention and its isomers, racemates, enantiomers, diastereomers, enantiomer enriched products, solvates, and esters can further form solvates, such as hydrates, alcohol adducts and etc. The above compounds can also be prodrugs or in the form that can release the active ingredient after metabolism in vivo. The selection and preparation of suitable prodrug derivatives is a well-known technique to a person skilled in the art. In general, with respect to the object of the invention, the form of solvate formed with a pharmaceutically acceptable solvent such as water and ethanol is equivalent to the form of non-solvate.

According to the invention, the compound of formula I of the invention can combine with a conventional pharmaceutically acceptable carriers or excipients to form a pharmaceutical composition. The pharmaceutical composition can be administered via oral or parenteral route. The pharmaceutical composition in the invention can be prepared according to conventional methods in the art into various dosage forms, including, but not limited to, tablets, capsules, solutions, suspensions, granules or injections, and administered via oral or parenteral route.

The term "composition" used herein is meant to indicate a product comprising various designated components in designated amounts, and any product produced directly or indirectly from the combination of various designated components in designated amounts.

By using a pharmaceutical vehicle as well known to a person skilled in the art, a pharmaceutical composition comprising an effective amount of the compound of the invention can be prepared. Thus, the invention further provides a pharmaceutical composition comprising the compound of the invention formulated together with one or more nontoxic pharmaceutically acceptable vehicle(s). The pharmaceutical composition can be especially formulated into the form of solid or liquid for oral administration, parenteral injection or rectal administration.

The pharmaceutical composition in the invention can be administered to human or other mammals via oral, rectal, parenteral, intracisternal, intravaginal, intraperitoneal, topical (such as via powders, ointments or drops) or buccal route, or as oral spray or nasal spray. The term "parenteral" used herein is meant to include the administration mode of intravenous, intramuscular, intraperitoneal, intrasternal, subcutaneous and intraarticular injection and infusion.

The composition suitable for parenteral injection may include physiologically acceptable sterile aqueous or non-aqueous solutions, dispersions, suspensions or emulsions, and sterile powders that can reconstitute sterile injectable solutions or dispersions. Suitable examples of aqueous or non-aqueous vehicle, diluent, solvent or medium include water, ethanol, polyhydric alcohol (such as propylene glycol, polyethylene glycol, glycerin), vegetable oil (such as olive oil), injectable organic esters such as ethyl oleate and suitable mixtures thereof.

The composition can also include auxiliary materials such as preservatives, wetting agents, emulsifying agents and dispersing agents. The use of various antibacterial agents and antifungal agents, such as paraben, trichloro-tert-butanol, phenol and sorbic acid, can ensure the effect of preventing microbes. It is also expected that isotonic agent such as saccharides and sodium chloride is further included. By using substances capable of delaying absorption, such as aluminum monostearate and gelatin, the prolonged absorption of injectable drug can be achieved.

The suspensions, in addition to active compound, can further include suspending agent, such as ethoxylated isooctadecanol, polyoxyethylene sorbitol and polyoxyethylene sorbitan carboxylic acid esters, microcrystalline cellulose, boehmite, bentonite, agar and tragacanth or mixtures thereof.

In some cases, in order to prolong the effect of drug, it is expected to slow down the absorption of drug for subcutaneous or intramuscular injection. This can be achieved by using a liquid suspension of crystal or amorphous substance having poor water solubility. Thus, the absorption rate of drug depends on its dissolution rate, while the dissolution rate may depend on the crystal size and form. Or, the delayed absorption of drug for parenteral administration can be achieved by dissolving or suspending the drug in an oil medium.

An injectable depot formulation can be prepared by forming a microcapsule matrix of drug in a biodegradable polymer such as polylactide-polyglycolide. The release rate of drug can be controlled according to the drug to polymer ratio and the property of the concrete polymer as used. Examples of other biodegradable polymers include poly(orthoesters) and poly(anhydrides). An injectable depot formulation can also be prepared by embedding drug in liposome or microemulsion that is compatible with body tissue.

An injectable formulation can be sterilized by, for example, filtering via a bacterial filter or incorporating a sterilizing agent in the form of sterile solid composition, and the solid composition can be dissolved or dispersed in sterile water or other sterile injectable medium before use.

The compound or its composition in the invention may be administered via oral or parenteral route. The formulation for oral administration may be in the form of tablets, capsules, coatings, and the formulation for parenteral administration may be in the form of injections, suppositories and etc. These formulations can be prepared according to methods as well known to a person skilled in the art. The auxiliary materials useful for preparing tablets, capsules and coatings are conventional ones, for example, starch, gelatin, Arabic gum, silica, polyethylene glycol, and the solvent useful for preparing liquid dosage forms includes, for example, water, ethanol, propylene glycol, vegetable oil (corn oil, peanut oil, olive oil and etc). The formulation comprising the compound of the invention further includes other auxiliary materials, for example, surfactants, lubricants, disintegrating agents, preservatives, correctants, pigments and etc. The dose of the compound of formula I of the invention in tablets, capsules, coatings, injections and suppositories is calculated as the amount of the compound present in unit dosage form. The compound of formula I of the invention is present in the unit dosage form in an amount of generally 1-5000 mg, preferably 10-500 mg, and more preferably 20-300 mg. In concrete, solid dosage forms for oral administration that can be provided in the invention include capsules, tablets, pills, powders and granules. In this type of solid dosage forms, active compound can be mixed with at least one inert pharmaceutically acceptable excipient or vehicle such as sodium citrate or dicalcium phosphate and/or the following substances: a) filling agent or bulking agent such as starch, lactose, sucrose, glucose, mannitol and silicic acid; b) binding agent such as carboxymethylcellulose, alginate, gelatin, polyvinylpyrrolidone, sucrose and Arabic gum; c) humectant such as glycerin; d) disintegrating agent such as agar, calcium carbonate, potato or tapioca starch, alginic acid, some silicates and sodium carbonate; e) solution retarder such as paraffin; f) absorption accelerator such as quaternary ammonium compound; g) wetting agent such as cetyl alcohol and glyceryl monostearate; h) adsorbent such as kaolin and bentonite; i) lubricant such as talc, calcium stearate, magnesium stearate, solid polyethylene glycol, sodium lauryl sulfate and mixtures thereof. In the case of being capsules, tablets and pills, the dosage form may also include buffering agent.

A similar type of solid composition, which employs excipient such as lactose and high molecular weight polyethylene glycol, can also be used as filler in soft capsules and solid capsules.

The solid formulations including tablets, dragees, capsules, pills and granules can be prepared along with coatings and shell materials such as enteric coating materials and other coating materials as well known in the field of pharmaceutical preparations. These solid formulations can optionally include opacifier, and their compositions can also enable them to merely or preferentially release active ingredient optionally in a delayed manner in certain sites of intestinal tract. Examples of useable embedding composition include polymeric substances and waxes. If appropriate, active compound can also be formulated into the form of microcapsules together with one or more of the aforesaid excipients.

Liquid dosage forms for oral administration include pharmaceutically acceptable emulsions, solutions, suspensions, syrups and elixirs. Liquid dosage forms can include, in addition to active compound, inert diluent as commonly used in the art, for example, water or other solvent, solubilizing agent and emulsifying agent such as ethanol, isopropanol, ethyl carbonate, ethyl acetate, benzyl alcohol, benzyl benzoate, propylene glycol, 1,3-butanediol, dimethylformamide, oils (in particular cottonseed oil, peanut oil, corn oil, embryo oil, olive oil, castor oil and sesame oil), glycerin, tetrahydrofurfuryl alcohol, polyethylene glycol and fatty acid esters of sorbitan and mixtures thereof. Compositions for oral administration can include, in addition to inert diluent, auxiliary materials such as wetting agent, emulsifying agent and suspending agent, sweetening agent, correctant and flavoring agents.

The composition for rectal or vaginal administration is preferably in the form of suppositories. Suppositories can be prepared by mixing the compound of the invention with a suitable non-stimulating excipient or vehicle such as cocoa butter, polyethylene glycol or wax for suppository. They are solid at room temperature, but are liquid at body temperature. Thus, they can melt in rectal lumen or vaginal canal to release active compound.

The compound and composition of the invention can also be used for topical administration. The dosage forms of the compound of the invention for topical administration include powders, sprays, ointments and inhalants. Under sterile conditions, active compound is mixed with a pharmaceutically acceptable vehicle and any desired preservative, buffering agent or propellant. Eye preparations, eye ointments, powders and solutions are also included in the scope of the invention.

The compound of the invention can also be administered in the form of liposome. As is well known in the art, liposome is generally prepared by using phospholipid or other lipid substances. Liposome is formed by monolayer or multilayer hydrated liquid crystal dispersed in aqueous medium. Any nontoxic, physiologically acceptable and metabolizable lipid capable of forming liposome can be used. The composition of the invention in the form of liposome can include, in addition to the compound of the invention, stabilizing agent, preservative, excipient and etc. Preferred lipids include natural and synthetic phospholipids and phosphatidylcholine (lecithin), which can be used alone or in combination. The method of forming liposome is well known in the art. Please refer to, for example, Prescott, Ed., Methods in Cell Biology, Volume XIV, Academic Press, New York, N.Y. (1976), p. 33.

When being used for the aforesaid treatment and/or prevention or for other treatment and/or prevention, a therapeutically and/or preventively effective amount of the compound of the invention can be used in pure form, or in the form of pharmaceutically acceptable esters or prodrugs (in case that these forms are present). Or, the compound can be administered in the form of pharmaceutical composition comprising the compound and one or more pharmaceutically acceptable excipient. The term "therapeutically and/or preventively effective amount" of the compound of the invention is meant to indicate a sufficient amount of the compound that is used for the treatment of impediment in a rational effect/risk ratio suitable for any medical treatment and/or prevention. However, it should be acknowledged that the total daily dose of the compound and composition of the invention must be determined by a chief doctor within a reliable medical judgment scope. As to any specific patient, the concrete therapeutically effective dosage level must be determined according to multiple factors. The factors include the impediment to be treated and the order of severity of the impediment; the activity of the concrete compound used; the concrete composition used; the age, body weight, natural health status, gender and nutrient status of the patient; the administration time, administration route and excretion rate of the concrete compound used; the duration of treatment; the drug that is used in combination or concurrently with the concrete compound used; and similar factors as well known in medical field. For example, the practice in this field includes starting from the use of compound at a dose that is lower than the level as required to obtain the desired therapeutic effect, and gradually increasing the dose until achieving the desired effect. In general, the dosage of the compound of formula I of the invention administered to mammals, in particular human, can be in the range of 0.001-1000 mg/kg body weight/day, for example, in the range of 0.01-100 mg/kg body weight/day, for example, in the range of 0.01-10 mg/kg body weight/day.

MODE OF CARRYING OUT THE INVENTION

The following examples are used to further illustrate the invention, and shall not be understood to limit the invention in any manner.

Preparation Example 1

Preparation of 6-chloro-2-(4-cyanophenylamino)-3-nitropyridine (IV-1)

2,6-Dichloro-3-nitropyridine (II-1, 193 mg, 1 mmol) and p-cyanophenylamine (III-1, 236 mg, 2 mmol) were dissolved in N,N-dimethylformamide (DMF, 3 mL). While cooling in ice bath, potassium t-butoxide (224 mg, 2 mmol) was added in batch, followed by reacting at room temperature for 2 h. The reaction solution was poured into ice water, and adjusted with diluted HCl to a pH of 5-6, followed by stirring for 30 min, to precipitate a solid. The solid was filtered out, washed with water until neutral, dried, and separated via a silica gel column (dichloromethane as eluant), to obtain compound IV-1 (186 mg, 68%), a pale yellow solid, mp 175-178° C. $^1$H NMR (CDCl$_3$) δ 10.47 (1H, br s, NH), 8.53 (1H, d, J=8.4 Hz, ArH-4), 7.86 (2H, d, J=8.8 Hz, ArH-2', 6'), 7.70 (2H, d, J=8.8 Hz, ArH-3', 5'), 6.96 (1H, d, J=8.4 Hz, ArH-5); MS (m/z): 275 (M$^+$).

Preparation Example 2

Preparation of 2-phenylamino-6-chloro-3-nitropyridine (IV-2)

2,6-dichloro-3-nitropyridine (II-1, 193 mg, 1 mmol), phenylamine (III-2, 93 mg, 1 mmol) and sodium bicarbonate (84 mg, 1 mmol) were added to 10 mL anhydrous ethanol, and reacted at room temperature for 24 h. The reaction solution was poured into ice water, and adjusted with diluted HCl to a pH of 5-6, followed by stirring for 30 min, to precipitate a solid. The solid was filtered out, washed with water until neutral, and then dried to obtain compound IV-2 (219 mg, 88), a red solid, mp 95-98° C. $^1$H NMR (CDCl$_3$) δ 10.28 (1H, b s, NH), 8.47 (1H, d, J=8.4 Hz, ArH-4), 7.66 (2H, d, J=8.0 Hz, ArH-2', 6'), 7.42 (2H, t, J=8.0 Hz, ArH-3', 5'), 7.21 (1H, t, J=7.2 Hz, ArH-4'), 6.81 (1H, d, J=8.4 Hz, ArH-5); MS (m/z): 250 (M$^+$).

Preparation Example 3

Preparation of 6-chloro-2-(4-methylphenylamino)-3-nitropyridine (IV-3)

The preparation method was the same as that used for preparing the compound IV-2, the yield being 49%. $^1$H NMR (CDCl$_3$) δ 10.22 (1H, br s, NH), 8.45 (1H, d, J=8.8 Hz, ArH-4), 7.30 (2H, d, J=8.4 Hz, ArH-2', 6'), 7.21 (2H, d, J=8.8 Hz, ArH-3', 5'), 6.77 (1H, d, J=8.8 Hz, ArH-5), 2.37 (3H, s, CH$_3$).

Preparation Example 4

Preparation of 6-chloro-2-(4-methoxyphenylamino)-3-nitropyridine (IV-4)

The preparation method was the same as that used for preparing the compound IV-2, the yield being 76%. $^1$H NMR (CDCl$_3$) δ 10.17 (1H, br s, NH), 8.45 (1H, d, J=8.8 Hz, ArH-4), 7.53 (2H, d, J=8.8 Hz, ArH-2', 6'), 6.95 (2H, d, J=8.8 Hz, ArH-3', 5'), 6.75 (1H, d, J=8.8 Hz, ArH-5), 3.84 (3H, s, CH$_3$); MS (m/z): 280 (M$^+$).

Preparation Example 5

Preparation of 6-chloro-2-(4-ethoxyphenylamino)-3-nitropyridine (IV-5)

The preparation method was the same as that used for preparing the compound IV-2, the yield being 86%. $^1$H NMR (CDCl$_3$) δ 10.16 (1H, br s, NH), 8.44 (1H, d, J=8.4 Hz, ArH-4), 7.52 (2H, d, J=8.8 Hz, ArH-2', 6'), 6.93 (2H, d, J=8.8 Hz, ArH-3', 5'), 6.75 (1H, d, J=8.4 Hz, ArH-5), 4.06 (2H, q, J=7.0 Hz, CH$_2$), 1.44 (3H, t, J=7.0 Hz, CH$_3$).

Example 1

Preparation of 2-(4-cyanophenylamino)-6-(2,6-dimethyl-4-bromophenoxy)-3-nitropyridine (I-1)

The compound IV-1 (274.5 mg, 1 mmol) and 4-bromo-2,6-dimethylphenol (241.2 mg, 1.2 mmol) were dissolved in 1 mL DMF, to which was added potassium carbonate (345 mg, 2.5 mmol). Under the protection of nitrogen, the system was reacted at 130° C. for 6 h. The reaction product was poured into ice water, and adjusted with diluted HCl to a pH of 5-6, followed by stirring for 30 min, to precipitate a solid. The solid was filtered out, washed with water, dried, and separated via a silica gel column, to obtain a yellow compound I-1 (280 mg, 64%). $^1$H NMR (CDCl$_3$) δ 10.65 (1H, br s, NH), 8.63 (1H, d, J=9.0 Hz, ArH-4), 7.37 (4H, m, ArH-3', 5', 3", 5"), 7.21 (2H, d, J=8.6 Hz, ArH-2', 6'), 6.65 (1H, d, J=9.0 Hz, ArH-5), 2.08 (6H, s, CH$_3$-2", CH$_3$-6"); MS (m/z): 439 (M$^+$).

Example 2

Preparation of 2-(4-cyanophenylamino)-6-(2,6-dimethyl-4-cyanophenoxy)-3-nitropyridine (I-2)

The preparation method was the same as that used for preparing the compound I-1, except for reacting the intermediate IV-1 (274.5 mg, 1 mmol) with 2,6-dimethyl-4-cyanophenol (147.6 mg, 1.2 mmol) to obtain the product I-2 (225 mg, 58%). $^1$H NMR (CDCl$_3$) δ 10.68 (1H, br s, NH), 8.66 (1H, d, J=8.8 Hz, ArH-4), 7.53 (2H, s, ArH-3', 5'), 7.32 (2H, d, J=8.3 Hz, ArH-3", 5"), 7.19 (2H, d, J=8.3 Hz, ArH-2", 6"), 6.67 (1H, d, J=9.2 Hz, ArH-5), 2.16 (6H, s, CH$_3$-2", CH$_3$-6"); MS (m/z) 386 (M$^+$)

Example 3

Preparation of 2-(4-cyanophenylamino)-6-(2,4,6-trimethylphenoxy)-3-nitropyridine (I-3)

The preparation method was the same as that used for preparing the compound I-1, except for reacting the intermediate IV-1 (274.5 mg, 1 mmol) with 2,4,6-trimethylphenol (163.2 mg, 1.2 mmol) to obtain the product I-3 (268.1 mg, 72%). $^1$H NMR (DMSO-d$_6$) δ 10.38 (1H, br s, NH), 8.65 (1H, d, J=8.8 Hz, ArH-4), 7.39 (4H, m, ArH-2', 3', 5', 6'), 7.04 (2H, s, ArH-3", 5"), 6.78 (1H, d, J=8.8 Hz, ArH-5), 2.36 (3H, CH$_3$-4"), 2.00 (s, CH$_3$-2", CH$_3$-6"); MS (m/z) 375 (M$^+$).

Example 4

Preparation of 2-(4-cyanophenylamino)-6-(2,6-dimethyl-4-formylphenoxy)-3-nitropyridine (I-4)

The preparation method was the same as that used for preparing the compound I-1, except for reacting the intermediate IV-1 (274.5 mg, 1 mmol) with 3,5-dimethyl-4-hydroxybenzaldehyde (180 mg, 1.2 mmol) to obtain the product I-4 (257 mg, 66%). $^1$H NMR (CDCl$_3$) δ 10.68 (1H, br s, NH), 10.08 (1H, s, CHO), 8.66 (1H, d, J=8.8 Hz, ArH-4), 7.75 (2H, s, ArH-3', 5'), 7.20 (4H, s, ArH-2", 3", 5", 6"), 6.69 (1H, d, J=9.2 Hz, ArH-5), 2.21 (6H, s, CH$_3$-2", CH$_3$-6"); MS (m/z) 389 (M$^+$).

Example 5

Preparation of 2-(4-cyanophenylamino)-6-(2,6-dimethyl-4-cyanovinylphenoxy)-3-nitropyridine (I-5)

(EtO)$_2$P(O)CH$_2$CN (265.7 mg, 1.5 mmol) was dissolved in 15 mL THF, while cooling in ice bath, potassium t-butoxide (168 mg, 1.5 mmol) was added, followed by stirring for 30 min. Then, the system was reacted at room temperature for 30 min. A solution of compound I-4 (388.4 mg, 1 mmol) dissolved in 15 mL THF was added to the system, and then reacted for 24 h. 100 mL water was added, followed by standing for 12 h. The reaction product was filtered out, and washed with water, to obtain a yellow solid I-5 (346 mg, 84%). $^1$H NMR (DMSO-d$_6$) δ 10.37 (1H, br s, NH), 8.68 (1H, d, J=8.8 Hz, ArH-4), 7.72 (1H, d, J=16.8 Hz, Ar—CH═C), 7.56 (2H, s, ArH-3", 5"), 7.34 (4H, s, ArH-2', 3', 5', 6'), 6.84 (1H, d, J=8.8 Hz, ArH-5), 6.53 (1H, J=16.8 Hz, —C═CHCN), 2.06 (6H, s, CH$_3$-2", CH$_3$-6"); MS (m/z) 412 (M$^+$).

Example 6

Preparation of 3-amino-2-(4-cyanophenylamino)-6-(2,6-dimethyl-4-cyanophenoxy)pyridine (I-6)

A mixture of the compound I-2 (385.4 mg, 1 mmol), 5 mL cyclohexene, 100 mL isopropanol and 100 mg 10% Pd/C was reacted under reflux conditions for 3-5 h, using TLC to show the end of the reaction. The reaction product was filtered while being hot, and the filtrate was concentrated and then separated by column chromatography (ethyl acetate and petroleum ether as eluant), to obtain a grey solid compound I-6 (235 mg, 66%). $^1$H NMR (DMSO-d$_6$) δ 8.36 (1H, br s, NH), 7.73 (2H, s, ArH-3', 5'), 7.32 (2H, d, J=9.2 Hz, ArH-3', 5'), 7.26 (2H, s, ArH-2', 6'), 7.14 (1H, d, J=8.0 Hz, ArH-4), 6.49 (1H, d, J=8.0 Hz, H-5), 4.88 (2H, br s, NH$_2$), 2.08 (6H, s, CH$_3$-2", CH$_3$-6"); MS (m/z): 356 (M$^+$).

Example 7

Preparation of 3-amino-2-(4-cyanophenylamino)-6-(2,6-dimethyl-4-hydroxyl-methylphenoxy)pyridine (I-7)

The compound I-4 (388.4 mg, 1 mmol) and NiCl$_2$.6H$_2$O (71 mg, 0.3 mmol) were dissolved in a mixed solution of 25 mL methanol and 25 mL THF with stirring, and then cooled in ice bath. When the temperature was lowered to less than 5° C., NaBH$_4$ (228 mg, 6 mmol) was added in batch. After reacting for 30 min, 50 mL water was added to the reaction solution. Then, the reaction solution was adjusted with 1 N HCl to a pH of 5-6. The ice bath was moved away, and then the reaction solution was heated to 50-60° C. After 10 min, the heating was stopped. Until being cooled down, the reaction solution was respectively extracted with 50 mL EtOAc for three times. The organic phases were combined, dried, concentrated, and then separated via a column to obtain the product I-7 (254 mg, 70%). $^1$H NMR (DMSO-d$_6$) δ 8.27 (1H, br s, NH), 7.34 (4H, s, ArH-2', 3', 5', 6'), 7.11 (1H, d, J=8.0 Hz, ArH-4), 7.10 (2H, s, ArH-3", 5"), 6.38 (1H, d, J=8.0 Hz, ArH-5), 5.22 (1H, t, J=6.4 Hz, OH), 4.76 (2H, br s, NH$_2$), 4.49 (2H, d, J=6.4 Hz, CH$_2$), 2.03 (6H, s, CH$_3$-2", CH$_3$-6"); MS (m/z) 361 (M$^+$).

Example 8

Preparation of 2-(4-cyanophenylamino)-6-(2,6-dimethyl-4-hydroxymethylphenoxy)-3-nitropyridine (I-8)

The compound I-4 (388.4 mg, 1 mmol) was dissolved in a mixed solution of 25 mL and 25 mL THF with stirring, and then cooled in ice bath. When the temperature was lowered to less than 5° C., NaBH$_4$ (114 mg, 4 mmol) was added in batch. After reacting for 30 min, 50 mL water was added to the reaction solution. Then, the reaction solution was adjusted with 1 N HCl to a pH of 5-6. The ice bath was moved away, and then the reaction solution was heated to 50-60° C. After 10 min, the heating was stopped. Until being cooled down, the reaction solution was respectively extracted with 50 mL EtOAc for three times. The organic phases were combined, dried, concentrated, and then separated via a column to obtain the product I-8 (286 mg, 73%). $^1$H NMR (DMSO-d$_6$) δ 10.41 (1H, br s, NH), 8.67 (1H, d, J=8.8 Hz, ArH-4), 7.45 (2H, d, J=8.8 Hz, ArH-3', 5'), 7.37 (2H, d, J=8.8 Hz, ArH-2', 6'), 7.19 (2H, s, ArH-3", 5"), 6.81 (1H, d, J=8.8 Hz, ArH-5), 5.39 (1H, t, J=6.4 Hz, OH), 4.55 (2H, d, J=6.4 Hz, CH$_2$), 2.04 (6H, s, CH$_3$-2", CH$_3$-6"); MS (m/z): 391 (M$^+$)

Example 9

Preparation of 2-(4-cyanophenylamino)-6-(2,6-dimethyl-4-allylphenoxy)-3-nitropyridine (I-9)

The preparation method was the same as that used for preparing the compound I-1, except for reacting the intermediate IV-1 (274.5 mg, 1 mmol) with 2,6-dimethyl-4-allylphenol (194.4 mg, 1.2 mmol) to obtain the product I-9 (225 mg, 56%). $^1$H NMR (CDCl$_3$) δ 10.67 (1H, br s, NH), 8.61 (1H, d, J=8.8 Hz, ArH-4), 7.27 (4H, m, ArH-2', 3', 5', 6'), 7.01 (2H, s, ArH-3", 5"), 6.63 (1H, d, J=8.8 Hz, ArH-5), 6.05 (1H, m, —CH=), 5.24 (2H, m, —CH$_2$—), 3.44 (1H, d, J=3.2 Hz, CH$_2$=), 2.08 (6H, s, CH$_3$-2", CH$_3$-6"); MS (m/z): 401 (M$^+$).

Example 10

Preparation of 3-amino-2-(4-cyanophenylamino)-6-(2,6-dimethyl-4-cyanovinylphenoxy)pyridine (I-10)

The compound I-5 (411.4 mg, 1 mmol) was added to a mixed solution of 30 mL 1,4-dioxane and 30 mL H$_2$O, to which were further added 1 mL aqueous ammonia, and Na$_2$S$_2$O$_4$ (1741 mg, 10 mmol), followed by stirring at room temperature for 2 h. The reaction solution was respectively extracted with 50 mL EtOAc for three times. The organic phases were combined, dried, concentrated, and then separated via a column to obtain the product I-10 (192 mg, 50%). $^1$H NMR (DMSO-d$_6$) δ 8.35 (1H, br s, NH), 7.68 (1H, J=16.8 Hz, Ar—CH=C), 7.50 (2H, s, ArH-3", 5"), 7.37 (2H, d, J=8.8 Hz, ArH-3', 5'), 7.25 (2H, d, J=8.8 Hz, ArH-2', 6'), 7.13 (1H, d, J=8.0 Hz, ArH-4), 6.45 (1H, d, J=8.0 Hz, ArH-5), 6.45 (1H, J=16.8 Hz, =CHCN), 2.06 (6H, s, CH$_3$-2", CH$_3$-6"). MS (m/z): 382 (M$^+$).

Example 11

Preparation of 2-(4-cyanophenylamino)-6-(2,6-dimethyl-4-methylphenylamino)-3-nitropyridine (I-11)

The compound IV-1 (274.5 mg, 1 mmol) and 2,4,6-trimethylphenylamine (810 mg, 6 mmol) were added in a microwave tube, to which were further added anhydrous potassium carbonate (483 mg, 3.5 mmol) and 3 mL t-BuOH. By heating with microwave, the system was reacted at 180° C. for 30 min. At the end of the reaction, the reaction solution was poured into ice water, and adjusted with 1 N HCl to a pH of 2-3, followed by stirring. The reaction product was filtered out, dried, and separated via a column to obtain a yellow solid, 267 mg, yield 72%. $^1$H NMR (DMSO-d$_6$) δ 10.80 (1H, br s, NH), 9.73 (1H, br s, NH), 8.29 (1H, d, J=9.2 Hz, ArH-4), 7.50 (2H, d, J=8.8 Hz, ArH-2', 6'), 7.31 (2H, d, J=8.8 Hz, ArH-3', 5'), 7.05 (2H, s, ArH-3", 5"), 6.47 (1H, d, J=9.2 Hz, ArH-5), 2.37 (3H, s, CH$_3$-4"), 2.08 (6H, s, CH$_3$-2", CH$_3$-6"); MS (m/z) 374 (M$^+$).

By reference to the above method for the preparation of the compound I-11 wherein X is —NH— or employing the compound I-11 as the starting compound, a person skilled in the art, in accordance with the knowledge he or she grasps and the method as well known in the art, can further obtain the compounds of formula I wherein X is —NR— and —NCOR—, wherein R is C$_{1-4}$ hydrocarbyl such as methyl, ethyl, propyl, and etc.

Example 12

Preparation of 3-amino-2-(4-cyanophenylamino)-6-(2,6-dimethyl-4-bromophenoxy)pyridine (I-12)

The preparation method was the same as that used for preparing the compound I-7, except for the reactant used being compound I-1 (439 mg, 1 mmol), to obtain a grey solid, 336 mg, yield 82%, mp 190-193° C. $^1$H-NMR (DMSO-d$_6$) δ 8.35 (1H, br s, NH), 7.42 (2H, s, ArH-3", 5"), 7.32 (4H, s, ArH-3', 4', 5', 6'), 7.12 (1H, d, J=8.0 Hz, ArH-4), 6.44 (1H, d, J=8.0 Hz, ArH-5), 4.84 (2H, br s, NH$_2$), 2.03 (6H, s, CH$_3$-2", CH$_3$-6"); MS (m/z): 409 (M$^+$).

Example 13

Preparation of 3-amino-2-(4-cyanophenylamino)-6-(2,6-dimethyl-4-allylphenoxy)pyridine (I-13)

The preparation method was the same as that used for preparing the compound I-10, except for the reactant used being compound I-9 (400 mg, 1 mmol), to obtain a grey solid, 160 mg, yield 43%, mp 150-152° C. $^1$H-NMR (DMSO-d$_6$) δ 8.30 (1H, br s, NH), 7.36 (2H, d, J=8.8 Hz, ArH-3', 5'), 7.29 (2H, d J=8.8 Hz, ArH-2', 6'), 7.11 (1H, d, J=8.0 Hz, ArH-4), 6.98 (2H, s, ArH-3", 5"), 6.39 (1H, d, J=8.0 Hz, ArH-5), 6.03 (1H, m, —CH=), 5.14 (2H, m, —CH$_2$—), 4.76 (2H, br s, NH$_2$), 3.36 (2H, d, J=3.6 Hz, CH$_2$=), 2.01 (6H, s, CH$_3$-2", CH$_3$-6"); MS (m/z) 371 (M$^+$).

Example 14

Preparation of 2-(4-cyanophenylamino)-6-(2,6-dimethyl-4-(1-hydroxy-2-nitroethyl)phenoxy)-3-nitropyridine (I-14)

388 mg (1 mmol) of the compound I-4 was dissolved in 20 mL THF, to which was added 2 mL CH$_3$NO$_2$. While stirring and cooling in ice bath, 1 mL of a 33% NaOH solution was added dropwise. At the end of the addition, the system was further stirred for 1 h, and then moved away to further react at room temperature for 12 h. After stopping the reaction, the reaction solution was poured into 50 mL ice water, and extracted with dichloromethane (25 mL×3). The organic phases were dried with anhydrous sodium sulfate, and concentrated. The resultant solid was separated via column chromatography (eluant: dichloromethane/methanol=60/1, silica gel of 200-300 meshes), to obtain a yellow solid, 306 mg, yield 68%, mp 230-234° C. $^1$H-NMR (DMSO-d$_6$) δ ppm 12.43 (1H, br s, NH), 8.68 (1H, d, J=8.0 Hz, ArH-4), 7.49 (2H, d, J=8.8 Hz, ArH-3', 5'), 7.40 (2H, d, J=8.4 Hz, ArH-2', 6'), 7.33 (2H, s, ArH-3", 5"), 6.81 (2H, d, J=8.8 Hz, ArH-5), 6.32 (1H, d, J=6.4 Hz, AOH), 5.33 (1H, m, CH$_2$NO$_2$<u>C</u>HOH), 4.94 (1H, m, CH$_2$NO$_2$), 4.66 (1H, m, <u>C</u>HOH), 2.06 (6H, s, CH$_3$-2", CH$_3$-6"); MS (m/z) 450 (M$^+$).

Example 15

Preparation of 2-(4-cyanophenylamino)-6-(2,6-dimethyl-4-(2-cyclopropylamino methyl)phenoxy)-3-nitropyridine (I-15)

388 mg (1 mmol) of the compound I-4 was dissolved in a mixed solution of 40 mL THF and 30 mL methanol, to which were added 228 mg (4 mmol) of cyclopropylamine and 1 mL triethylamine, followed by stirring and refluxing for 4 days. After stopping the reaction, the reaction solution was cooled in ice bath, to which 151 mg (4 mmol) of NaBH$_4$ was added in batch, followed by stirring for 30 min. After stopping the reaction, the reaction solution was poured into 100 mL ice water, adjusted with HCl (1N) to a pH of 4-5, and heated to 40-50° C., followed by stirring for 10 min. The reaction solution was extracted with ethyl acetate (20 mL×3). The organic phases were dried with anhydrous sodium sulfate, and concentrated. The resultant solid was separated via flash chromatography (eluant: ethyl acetate/petroleum ether, 0-50% gradient elution), to obtain a yellow solid, 92 mg, yield 21%, mp 175-177° C. $^1$H-NMR δ ppm 10.68 (1H, br s, NH), 8.61 (1H, d, J=9.2 Hz, ArH-4), 7.31 (2H, d, J=8.8 Hz, ArH-3', ArH-5'), 7.26 (2H, d, J=8.8 Hz, ArH-2', ArH-6'), 7.14 (2H, s, ArH-3", ArH-5"), 6.63 (1H, d, J=9.2 Hz, ArH-5), 3.90 (2H, s, CH$_2$), 2.10 (6H, s, CH$_3$-2", CH$_3$-6"), 0.52 (4H, m, CH$_2$, CH$_2$); MS (m/z) 430 (M$^+$).

Example 16

Preparation of 2-(4-cyanophenylamino)-6-(2,6-dimethyl-4-iodophenoxy)-3-nitropyridine (I-16)

The preparation method was the same as that used for preparing the compound I-1, except for reacting the intermediate IV-1 (274.5 mg, 1 mmol) with 2,6-dimethyl-4-iodophenol (297 mg, 1.2 mmol) to obtain the product I-16 (399 mg, 82%), mp 162-165° C. $^1$H-NMR (CDCl$_3$) δ 10.65 (1H, br s, NH), 8.63 (1H, d, J=8.8 Hz, ArH-4), 7.54 (2H, s, ArH-3", 5"), 7.38 (2H, d, J=8.8 Hz, ArH-3', 5'), 7.21 (2H, d, J=8.8 Hz, ArH-2', 6'), 6.65 (1H, d, J=8.8 Hz, ArH-5), 2.06 (6H, s, CH$_3$-2", CH$_3$-6"); MS (m/z): 487 (M$^+$).

Example 17

Preparation of 2-(4-cyanophenylamino)-6-(2,6-dimethyl-4-nitrophenoxy)-3-nitropyridine (I-17)

The preparation method was the same as that used for preparing the compound I-1, except for reacting the intermediate IV-1 (274.5 mg, 1 mmol) with 2,6-dimethyl-4-nitrophenol (200 mg, 1.2 mmol) to obtain the product I-17 (271 mg, 63%), mp 250-252° C. $^1$H-NMR (CDCl$_3$) δ 10.98 (1H, br s, NH), 8.68 (1H, d, J=9.2 Hz, ArH-4), 8.10 (2H, s, ArH-3", 5"), 7.26 (2H, d, J=8.8 Hz, ArH-3', 5'), 7.20 (2H, d, J=8.8 Hz, ArH-2', 6'), 6.70 (1H, d, J=9.2 Hz, ArH-5), 2.23 (6H, s, CH$_3$-2", CH$_3$-6"); MS (m/z) 406 (M$^+$).

Example 18

Preparation of 2-(4-cyanophenylamino)-6-(2,6-dimethyl-4-(3-methyl-3-hydroxy-1-butynyl)phenoxy)-3-nitropyridine (I-18)

486 mg (1 mmol) of the compound I-16 was dissolved in 5 mL DMF, to which were added 69 mg (0.1 mmol) Pd(PPh$_3$)$_2$Cl$_2$, 19 mg CuI (0.1 mmol), and 0.6 mL triethylamine, under the protection of N$_2$, with stirring. At room temperature, 420 mg (5 mmol) 2-methyl-2-hydroxy-3-butyne was added to the system, followed by stirring for 7 h. After stopping the reaction, 30 mL water was added to the reaction solution, which was then extracted with dichloromethane (25 mL×3). The organic phases were dried with anhydrous sodium sulfate, and concentrated. The resulting crude product was separated via flash chromatography (eluant: ethyl acetate/petroleum ether, 0-40% gradient elution), to obtain a yellow solid, 362 mg, yield 78%, mp 114-116° C. $^1$H-NMR (DMSO-d$_6$) δ 10.37 (1H, br s, NH), 8.67 (1H, d, J=8.8 Hz, ArH-4), 7.40 (2H, d, J=8.8 Hz, ArH-2', 6'), 7.34 (2H, d, J=8.8 Hz, ArH-3', 5'), 7.31 (2H, s, ArH-3", 5"), 6.83 (1H, d, J=8.8 Hz, ArH-5), 5.47 (1H, s, OH), 2.00 (6H, s, CH$_3$-2", CH$_3$-6"), 1.53 (6H, s, C≡C—C(CH$_3$)$_2$OH); MS (m/z): 465 (M+Na$^+$).

Example 19

Preparation of 6-(2,6-dimethyl-4-(3-methyl-3-hydroxy-1-butynyl)ethynylphenoxy)-2-(4-cyanophenylamino)-3-aminopyridine (I-19)

442 mg (1 mmol) of the compound I-18 was added to 20 mL THF, to which were added 20 mL water, and 0.5 mL aqueous ammonia. While stirring at room temperature, 1.93 g (content 90%, 10 mmol) Na$_2$S$_2$O$_4$ was added, followed by further stirring for 2 h, using TLC (dichloromethane/methanol=15/1) to show the end of the reaction. The reaction solution was poured into 100 mL water, and extracted with ethyl acetate (50 mL×3). The organic phases were dried with anhydrous sodium sulfate, concentrated, and then separated via column chromatography (eluant: dichloromethane/methanol=30/1, silica gel of 200-300 meshes), to obtain a grey solid, 198 mg, yield 48%, mp 155-157° C. $^1$H-NMR (DMSO-d$_6$) δ 8.33 (1H, br s, NH), 8.01 (1H, br s, OH), 7.41 (1H, d, J=8.8 Hz, ArH-4), 7.29 (4H, m, ArH-2', 3', 5', 6'), 7.23 (2H, s, ArH-3", 5"), 6.55 (1H, d, J=8.8 Hz, ArH-5), 4.83 (2H, br s, NH$_2$), 2.08 (6H, s, CH$_3$-2", CH$_3$-6"), 1.51 (6H, s, C≡C—C(CH$_3$)$_2$OH); MS (m/z) 413 (M$^+$).

Example 20

Preparation of 2-(4-cyanophenylamino)-6-(2,6-dimethyl-4-(cyclopropylethynyl)phenoxy)-3-nitropyridine (I-20)

486 mg (1 mmol) of the compound I-16 was dissolved in 5 mL DMF, to which were added 69 mg (0.1 mmol) Pd(PPh$_3$)$_2$Cl$_2$, 19 mg CuI (0.1 mmol) and 0.6 mL triethylamine, under the protection of N$_2$, with stirring. At room temperature, 330 mg (5 mmol) of cyclopropyne was added, followed by stirring for 7 h. After stopping the reaction, 30 mL water was added to the reaction solution, which was then extracted with dichloromethane (25 mL×3). The organic phases were dried with anhydrous sodium sulfate, and concentrated. The resultant crude product was separated via flash chromatography (eluant: ethyl acetate/petroleum ether, 0-40% gradient elution), to obtain a yellow solid, 290 mg, yield 68%, mp 188-192° C. $^1$H-NMR (CDCl$_3$) δ 10.65 (1H, br s, NH), 8.61 (1H, d, J=9.2 Hz, ArH-4), 7.36 (2H, d, J=8.8 Hz, ArH-3', 5'), 7.22 (2H, s, ArH-3", 5"), 7.19 (2H, d, J=8.8 Hz, ArH-2', 6'), 6.64 (1H, d, J=9.2 Hz, ArH-5), 2.05 (6H, s, CH$_3$-2", CH$_3$-6"), 1.52 (1H, m, CH), 0.89 (4H, m, 2×CH$_2$); MS (m/z) 425 (M$^+$).

Example 21

Preparation of 3-amino-2-(4-cyanophenylamino)-6-(2,6-dimethyl-4-(cyclopropylethynyl)phenoxy)pyridine (I-21)

424 mg (1 mmol) of the compound I-20 was added to 20 mL THF, to which were added 20 mL water, and 0.5 mL aqueous ammonia. While stirring at room temperature, 1.93 g (content 90%, 10 mmol) Na$_2$S$_2$O$_4$ was added, followed by further stirring for 2 h, using TLC (dichloromethane/methanol=15/1) to show the end of the reaction. The reaction solution was poured into 100 mL water, and extracted with ethyl acetate (50 mL×3). The organic phases were dried with anhydrous sodium sulfate, and concentrated, and then separated via column chromatography (eluant: dichloromethane/methanol=30/1, silica gel of 200-300 meshes), to obtain a grey solid, 193 mg, yield 49%, mp 82-85° C. $^1$H-NMR (CDCl$_3$) δ 7.33 (2H, d, J=8.4 Hz, ArH-3', 5') 7.22 (2H, s, ArH-3", 5"), 7.18 (3H, m, ArH-2', 6', 4), 6.36 (1H, d, J=8.0 Hz, ArH-5), 2.06 (6H, s, CH$_3$-2", CH$_3$-6"), 1.51 (1H, m, CH), 0.89 (4H, m, 2×CH$_2$); MS (m/z) 395 (M$^+$).

Example 22

Preparation of 2-(4-cyanophenylamino)-6-(2,6-dimethyl-4-ethynylphenoxy)-3-nitropyridine (I-22)

442 mg (1 mmol) of the compound I-18 was dissolved in 20 mL toluene, to which was added 16 mg (0.4 mmol) NaOH (fully ground), followed by, under the protection of N$_2$, refluxing for 24 h. After stopping the reaction, 2 drops of acetic acid was added to the reaction solution as cooled down, and the solvent was removed by vacuum distillation. The resultant solid was separated via flash chromatography (eluant: ethyl acetate/petroleum ether, 0-40% gradient elution), to obtain a yellow solid, 265 mg, yield 69%, mp 186-188° C. $^1$H-NMR (CDCl$_3$) δ 10.66 (1H, br s, NH), 8.63 (1H, d, J=8.8 Hz, ArH-4), 7.35 (2H, d, J=8.8 Hz, ArH-3', 5'), 7.34 (2H, s, ArH-3", 5"), 7.19 (2H, d, J=8.8 Hz, ArH-2', 6'), 6.66 (1H, d, J=8.8 Hz, ArH-5), 3.17 (1H, s, C≡CH), 2.09 (6H, s, CH$_3$-2", CH$_3$-6"); MS (m/z) 385 (M$^+$).

Example 23

Preparation of 3-amino-2-(4-cyanophenylamino)-6-(2,6-dimethyl-4-ethynylphenoxy)pyridine (I-23)

384 mg (1 mmol) of the compound I-22 was added to 20 mL THF, to which were added 20 mL water, and 0.5 mL aqueous ammonia. While stirring at room temperature, 1.93 g (content 90%, 10 mmol) Na$_2$S$_2$O$_4$ was added, followed by further stirring for 2 h, using TLC (dichloromethane/methanol=15/1) to show the end of the reaction. The reaction solution was poured into 100 mL water, and extracted with ethyl acetate (50 mL×3). The organic phases were dried with anhydrous sodium sulfate, and concentrated. The resultant solid was separated via flash chromatography (eluant: ethyl acetate/petroleum ether, 0-60% gradient elution), to obtain a grey solid, 217 mg, yield 61%, mp 79-82° C. $^1$H-NMR (DMSO-d$_6$) δ 8.34 (1H, br s, NH), 7.37 (2H, s, ArH-3", 5"), 7.03 (4H, m, ArH-2', 3', 5', 6'), 6.56 (1H, d, J=8.4 Hz, ArH-4), 6.44 (1H, d, J=8.4 Hz, ArH-5), 4.84 (2H, br s, NH$_2$), 3.36 (1H, s, CH), 2.02 (6H, s, CH$_3$-2", CH$_3$-6"); MS (m/z) 355 (M$^+$).

Example 24

Preparation of 3-amino-2-(4-cyanophenylamino)-6-(2,6-dimethyl-4-aminophenoxy)pyridine (I-24)

The preparation method was the same as that used for preparing the compound I-4, except for the reactant used being the compound I-17 (405 mg, 1 mmol), to obtain a grey solid, 210 mg, yield 61%, mp 195-198° C. $^1$H-NMR (CDCl$_3$) δ 8.29 (1H, br s, NH), 7.47 (2H, d, J=8.8 Hz, ArH-3', 5'), 7.39 (2H, d, J=8.8 Hz, ArH-2', 6'), 7.07 (1H, d, J=8.0 Hz, ArH-4), 6.35 (2H, s, ArH-3", 5"), 6.30 (1H, d, J=8.0 Hz, ArH-5), 4.88 (2H, br s, NH$_2$), 4.73 (2H, br s, NH$_2$), 1.89 (6H, s, CH$_3$-2", CH$_3$-6"); MS (m/z) 346 (M$^+$).

Example 25

Preparation of 3-amino-2-(4-cyanophenylamino)-6-(2,6-dimethyl-4-iodophenoxy)pyridine (I-25)

The preparation method was the same as that used for preparing the compound I-10, except for the reactant used being the compound I-16 (486 mg, 1 mmol), to obtain a grey solid, 225 mg, yield 49%, mp 186-188° C. $^1$H-NMR (CDCl$_3$) δ 7.50 (2H, s, NH$_2$), 7.33 (2H, d, J=8.8 Hz, ArH-3', 5'), 7.22 (2H, d, J=8.8 Hz, ArH-2', 6'), 6.98 (1H, d, J=8.4 Hz, ArH-4), 6.44 (1H, d, J=8.4 Hz, ArH-5), 2.09 (6H, s, CH$_3$-2", CH$_3$-6"); MS (m/z) 357 (M$^+$).

Example 26

Preparation of 2-(4-cyanophenylamino)-6-(2,4,6-tribromophenoxy)-3-nitropyridine (I-26)

The preparation method was the same as that used for preparing the compound I-1, except for reacting the intermediate IV-1 (274.5 mg, 1 mmol) with 2,4,6-tribromophenol (397 mg, 1.2 mmol) to obtain a yellow solid, 380 mg, yield 67%, mp 188-191° C. $^1$H-NMR (CDCl$_3$) δ 10.57 (1H, br s, NH), 8.68 (1H, d, J=8.8 Hz, ArH-4), 7.83 (2H, s, ArH-3", 5"), 7.38 (2H, d, J=8.8 Hz, ArH-3', 5'), 7.24 (2H, d, J=8.8 Hz, ArH-2', 6'), 6.72 (1H, d, J=8.8 Hz, ArH-5); MS (m/z) 569 (M$^+$).

Example 27

Preparation of 2-(4-cyanophenylamino)-6-(2,6-dibromo-4-formylphenoxy)-3-nitropyridine (I-27)

The preparation method was the same as that used for preparing the compound I-1, except for reacting the intermediate IV-1 (275 mg, 1 mmol) with 3,5-dibromo-4-hydroxybenzaldehyde (336 mg, 1.2 mmol) to obtain a yellow solid, 251 mg, yield 48%, mp 218-220° C. $^1$H-NMR (CDCl$_3$) δ 10.58 (1H, br s, NH), 10.03 (1H, s, CHO), 8.71 (1H, d, J=9.2 Hz, ArH-4), 8.18 (2H, s, ArH-3", 5"), 7.25 (4H, m, ArH-2', 3', 5', 6'), 6.76 (1H, d, J=9.2 Hz, ArH-5); MS (m/z) 519 (M$^+$).

Example 28

Preparation of 2-(4-cyanophenylamino)-6-(2,6-dibromo-4-hydroxymethylphenoxy)-3-nitropyridine (I-28)

The preparation method was the same as that used for preparing the compound I-1, except for reacting the intermediate IV-1 (274.5 mg, 1 mmol) with 2,6-dibromo-4-hydroxymethylphenol (338 mg, 1.2 mmol) to obtain a yellow solid, 271 mg, yield 52%, mp 209-213° C. $^1$H-NMR (CDCl$_3$) δ 10.57 (1H, br s, NH), 8.67 (1H, d, J=9.2 Hz, ArH-4), 7.69 (2H, s, ArH-3", 5"), 7.36 (2H, d, J=8.8 Hz, ArH-3', 5'), 7.26 (2H, d, J=8.8 Hz, ArH-2', 6'), 6.73 (1H, d, J=9.2 Hz, ArH-5), 4.81 (2H, s, CH$_2$); MS (m/z) 521 (M$^+$).

Example 29

Preparation of 2-(4-cyanophenylamino)-6-(2,6-difluorophenoxy)-3-nitropyridine (I-29)

The preparation method was the same as that used for preparing the compound I-1, except for reacting the intermediate IV-1 (274.5 mg, 1 mmol) with 2,6-difluorophenol (156 mg, 1.2 mmol) to obtain a yellow solid, 162 mg, yield 44%, mp 234-236° C. $^1$H-NMR (CDCl$_3$) δ 10.64 (1H, br s, NH), 8.66 (1H, d, J=8.8 Hz, ArH-4), 7.33 (5H, m, ArH-2', 3', 5', 6', 4"), 7.11 (2H, m, ArH-3", 4", 5"), 6.73 (1H, d, J=8.8 Hz, ArH-5); MS (m/z) 369 (M$^+$).

Example 30

Preparation of 2-(4-cyanophenylamino)-6-(2,6-dibromo-4-cyanovinylphenoxy)-3-nitropyridine (I-30)

The preparation method was the same as that used for preparing the compound I-5, except for the reactant used being the compound I-27 (518 mg, 1 mmol), to obtain a yellow solid, 363 mg, yield 67%, mp 223-226° C. $^1$H-NMR (DMSO-d$_6$) δ 10.31 (1H, br s, NH), 8.72 (1H, d, J=8.8 Hz, ArH-4), 8.17 (2H, s, ArH-3", 5"), 7.71 (1H, d, J=16.4 Hz, Ar—CH=C), 7.44 (2H, d, J=8.4 Hz, ArH-3', 5'), 7.36 (2H, d, J=8.4 Hz, ArH-2', 6'), 6.94 (1H, d, J=8.8 Hz, ArH-5), 6.76 (1H, d, J=16.4 Hz, —C=CHCN); MS (m/z) 540 (M$^+$).

The compound I-30 (539 mg, 1 mmol) was dissolved in acetone, and then a solution of HCl-ethyl ether was dropped slowly therein, to precipitate a yellow crystal, which was filtered, to obtain a hydrochloride salt of the compound I-30.

Example 31

Anti-HIV Activity Test (H9 Cell Model)

Please refer to the document (*J. Med. Chem.* 2004, 47, 756-760). Lymphocytes H9 were cultivated in culture medium 1640, under the conditions of 5% CO$_2$, 37° C. The test compound was initially dissolved in DMSO, and then diluted with culture medium to conventional screening concentrations: 100, 20, 4, 0.8 μg/mL. The cultivated H9 cells were divided into two portions, one of which was infected with HIV virus (IIIB) (m.i.o. 0.1-0.01 infectious Units/cell), and used for the determination of activity. Another portion of the cells, in which no virus, but merely culture medium was added, was used for the determination of toxicity. After having been cultivated under completely the same conditions (37° C., 5% CO$_2$) for 4 h, the two portions of cells were washed with fresh culture medium for 3 times, and then respectively added to different concentrations of test samples as formulated or to blank culture medium (the latter is positive infection control or negative drug control), while using AZT as positive drug control. All of these cells were cultivated under the conditions of 5% CO$_2$, 37° C. for 4 days. On the 4$^{th}$ day, the cell membranes of the cells infected with virus were firstly removed, and the cytosol was tested by using P24 antigen ELISA assay to determine the activity of the samples, which was expressed as EC$_{50}$. EC$_{50}$ meant an effective concentration at which 50% of virus replication was inhibited. The portion of cells in which no virus was added was tested by using cytometry to determine the toxicity of the samples, which was expressed as CC$_{50}$. CC$_{50}$ meant a concentration at which 50% of living cells were killed.

Example 32

Anti-HIV Activity Test (MT-2 Cell Model)

Please refer to the document (Jiang, S., et al. Antimicrob. Agents Chemother. 2004, 48, 4349-4359). In a 96-pore cell culture plate, 50 μl of different concentrations of compound solutions were respectively mixed with equal-volume of HIV-1$_{IIIB}$ virus strain (100 TCID$_{50}$), and incubated at 37° C. for 30 min, and then 100 μl MT-2 cell (1×10$^5$/mL, RPIM 1640 culture medium containing 10% serum) was added, and mixed homogenously, followed by incubation at 37° C. overnight. On the second day, 150 μl of the supernatant was sucked out, and equal-volume of fresh culture medium was replenished, followed by further incubation at 37° C. for 3 days. On the 4$^{th}$ day, cytopathic effect (CPE) was recorded. Thereafter, 100 μl of culture supernatant was sucked out, virus particles were split using 5% Triton X-100, and p24 antigen therein was tested by using ELISA assay. Briefly, a ELISA plate was coated with HIVIG (2 μg/mL), and blocked with 1% fat-free milk, then a virus lysate was added therein, followed by incubation at 37° C. for 60 min. After fully washing the plate, anti-p24 monoclonal antibody-183-12H-5C, biotin-labeled goat antimouse antibody and albumin-labeled horseradish peroxidase were added in sequence. Then, after developing with TMB, OD was tested at 450 nm. The 50% effective concentration (EC$_{50}$) of the compound was calculated using CalcuSyn software.

Example 33

Cytotoxicity Test of the Compound

Please refer to the document (Jiang, S., et al. Antimicrob. Agents Chemother. 2004, 48, 4349-4359). In a 96-pore cell culture plate, 50 μl of different concentrations of compound solutions were respectively mixed with equal-volume of PBS, and incubated at 37° C. for 30 min, and then 100 μl MT-2 (or H9) cells (1×10$^5$/mL, RPIM 1640 culture medium containing 10% serum) was added, and mixed homogenously, followed by incubation at 37° C. overnight. On the second day, 150 μl of the supernatant was sucked out, and equal-volume of fresh culture medium was replenished, followed by further incubation at 37° C. for 3 days. On the 4$^{th}$ day, 50 μl of a XTT solution (1 mg/mL) containing PMS as freshly prepared was added. After 4 h, OD at 450 nm was tested. The 50% cytotoxicity concentration (CC$_{50}$) of the compound was calculated using CalcuSyn software.

The results for biological assessment of partial compounds were listed in Table 1:

TABLE 1

Anti-HIV activity test data (H9 and MT-2 cells)

| Compound No. | Cell line | CC$_{50}$(μg/mL) | EC$_{50}$(μg/mL) | SI(CC$_{50}$/EC$_{50}$) |
|---|---|---|---|---|
| I-1 | H9 | 19.35 | <0.025 | >774 |
|  | MT-2 | 32.24 | 0.52 | 62 |
| I-2 | H9 | >25 | 0.0025 | >10,000 |
|  | MT-2 | 19.30 | 0.052 | 371 |
| I-3 | MT-2 | 503.18 | 0.118 | 4,264 |
| I-5 | MT-2 | 24.78 | 0.005 | 4,956 |
| I-6 | MT-2 | 11.28 | 0.0005 | 22,560 |
| I-7 | MT-2 | 0.79 | 0.002 | 394 |
| I-8 | MT-2 | 45.16 | 0.075 | 602 |
| I-9 | MT-2 | >100 | 0.109 | >917 |
| I-10 | MT-2 | 27.95 | 0.0042 | 6,656 |
| I-12 | MT-2 | 5.44 | 0.021 | 259 |
| I-13 | MT-2 | 2.13 | 0.09 | 24 |
| I-14 | MT-2 | 12.15 | 0.77 | 16 |
| I-16 | MT-2 | 72.19 | 1.18 | 61 |
| I-22 | MT-2 | 66.66 | 0.26 | 256 |
| I-23 | MT-2 | 2.92 | 0.15 | 19 |
| I-25 | MT-2 | 10.71 | 0.036 | 298 |
| I-26 | MT-2 | 26.97 | 0.179 | 151 |
| I-27 | MT-2 | 0.78 | 0.152 | 220 |

TABLE 1-continued

Anti-HIV activity test data (H9 and MT-2 cells)

| Compound No. | Cell line | $CC_{50}(\mu g/mL)$ | $EC_{50}(\mu g/mL)$ | $SI(CC_{50}/EC_{50})$ |
|---|---|---|---|---|
| I-28 | MT-2 | 36.32 | 0.253 | 145 |
| I-29 | MT-2 | 39.70 | 15.90 | 2 |
| I-30 | MT-2 | 24.80 | 0.045 | 551 |

SI: Selectivity index of compound, i.e., a ratio of toxicity $CC_{50}$ value to activity $EC_{50}$ value.

The compounds in other examples of the invention that are not listed in the above table also had $CC_{50}$, $EC_{50}$, and SI values that are similar to those of most compounds in the above table.

The results in the invention demonstrate that: the compound of formula I in the invention is a type of anti-HIV active compound having new backbone structure. Since this type of compound has relatively good molecular flexibility, the compound of the invention exhibits protent inhibitory activity to drug resistant HIV virus strain, and has prospects to develop into a new type of anti-HIV drug having new structure.

The invention claimed is:

1. A compound of formula Ia:

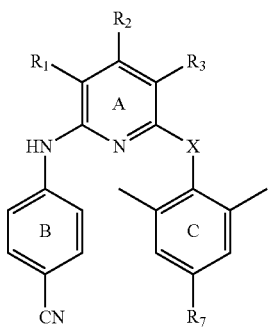

Ia or a pharmaceutically acceptable salt thereof,
wherein, $R_1$ and $R_3$ are each independently —$NO_2$, —$NH_2$, halo, —OH, —CN or —$N(R)_2$;

$R_2$ is —H;

$R_7$ is —CN, —HC═CH—CN, halo, —$CH_3$, —$OCH_3$, —$NH_2$, —$CH_2$—NHR', —OH, —$NO_2$, —$CF_3$, —C≡CR', —CH═CHR', —CH═CHCOR', —CHO, —C≡CR", —CH═CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;

R' is H or $C_{1-6}$ hydrocarbyl; R" is $NO_2$, $NH_2$, or $N_3$;

X is —O—, —NH— or —NCOR—; and

R is $C_{1-4}$ hydrocarbyl.

2. A method for preparing a compound according to claim 1, the reaction route being shown as follows:

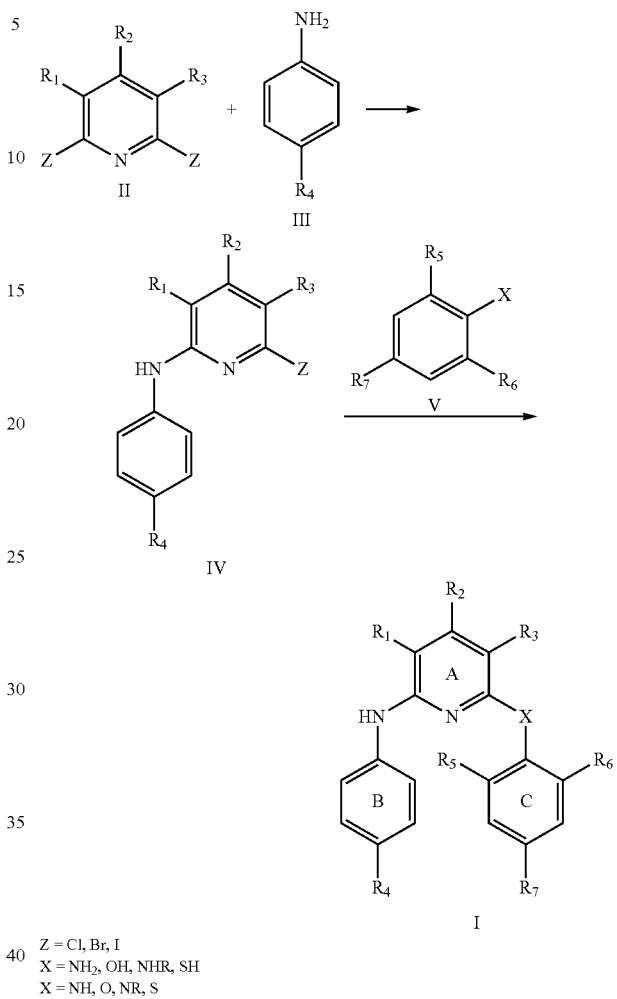

Z = Cl, Br, I
X = $NH_2$, OH, NHR, SH
X = NH, O, NR, S wherein $R_1$, $R_2$, $R_3$, $R_7$, and X are the same as defined for the compound of formula Ia in claim 2, $R_4$ is —CN, $R_5$ and $R_6$ are each —$CH_3$; the method comprises reacting a substituted 2,6-dihalopyridine compound of formula II with a para-substituted phenylamine compound of formula III under the action of a base, or reacting in the absence of solvent, to form a 2-(4-substituted phenylamino) polysubstituted pyridine compound of formula IV; thereafter, coupling the intermediate of formula IV with a polysubstituted phenol or phenylamine compound of formula V, or heating in the presence of palladium catalysts or coupling under microwave condition, to form a 2-(4-substituted phenylamino) polysubstituted pyridine compound of formula I.

3. A pharmaceutical composition, comprising a compound or a pharmaceutically acceptable salt thereof of claim 1 and one or more pharmaceutically acceptable carriers or excipients.

4. A method of treating diseases or conditions associated with HIV infection, comprising administering to a subject in need thereof a therapeutically effective amount of a compound or a pharmaceutically acceptable salt thereof of claim 1.

5. A compound of formula Ia:

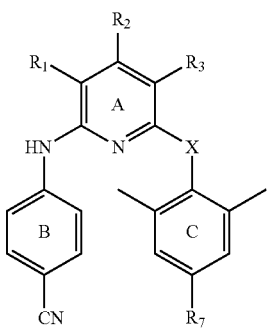

or a pharmaceutically acceptable salt thereof,
wherein, $R_1$ is —$NO_2$, —$NH_2$, halo, —OH, —CN or —$N(R)_2$;

$R_2$ and $R_3$ are —H;

$R_7$ is —CN, —HC=CH—CN, halo, —$CH_3$, —$OCH_3$, —$NH_2$, —$CH_2$—NHR', —OH, —$NO_2$, —$CF_3$, —CH=CHCOR', —C≡CR', —CH=CHR', —CHO, —C≡CR", —CH=CHR", —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;

R' is H or $C_{1-6}$ hydrocarbyl; R" is $NO_2$, $NH_2$, or $N_3$;

X is —O—, —NH— or —NCOR—; and

R is $C_{1-4}$ hydrocarbyl.

6. A method for preparing a compound according to claim 5, the reaction route being shown as follows:

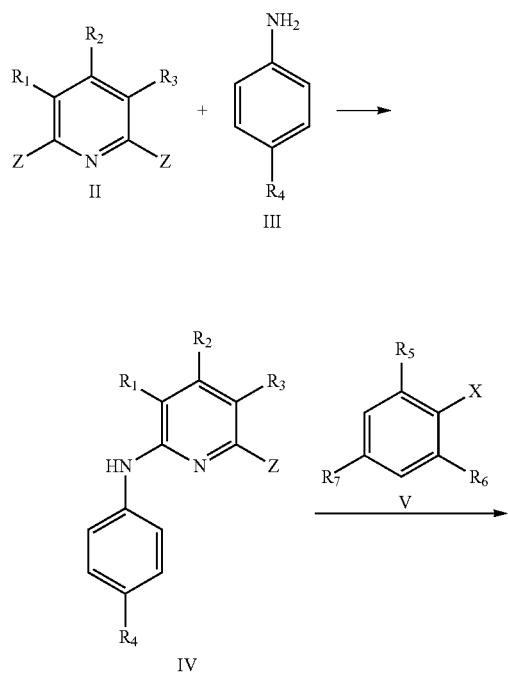

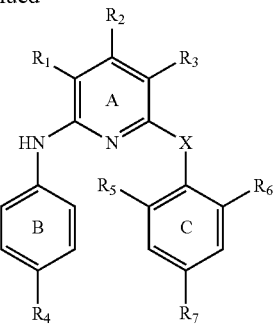

Z = Cl, Br, I
X = $NH_2$, OH, NHR, SH
X = NH, O, NR, S wherein $R_1$, $R_2$, $R_3$, $R_7$, and X are the same as defined for the compound of formula Ia in claim 3, $R_4$ is —CN, $R_5$ and $R_6$ are each —$CH_3$; the method comprises reacting a substituted 2,6-dihalopyridine compound of formula II with a para-substituted phenylamine compound of formula III under the action of a base, or reacting in the absence of solvent, to form a 2-(4-substituted phenylamino) polysubstituted pyridine compound of formula IV; thereafter, coupling the intermediate of formula IV with a polysubstituted phenol or phenylamine compound of formula V, or heating in the presence of palladium catalysts or coupling under microwave condition, to form a 2-(4-substituted phenylamino) polysubstituted pyridine compound of formula I.

7. A pharmaceutical composition, comprising a compound or a pharmaceutically acceptable salt thereof of claim 5 and one or more pharmaceutically acceptable carriers or excipients.

8. A method of treating diseases or conditions associated with HIV infection, comprising administering to a subject in need thereof a therapeutically effective amount of a compound or a pharmaceutically acceptable salt thereof of claim 5.

9. A compound of formula Ia:

Ia or a pharmaceutically acceptable salt thereof,
wherein, $R_1$ is —$NO_2$, or —$NH_2$;

$R_2$ and $R_3$ are —H;

$R_5$ and $R_6$ are each independently halo, $C_{1-6}$ alkyl, $C_{1-6}$ alkoxy, —$CF_3$, —$NH_2$, —OH, —COOH, —$NO_2$, —CN, or —H;

$R_7$ is —CN, —HC=CH—CN, halo, —CH$_3$, —OCH$_3$, —NH$_2$, —CH$_2$—NHR', —OH, —NO$_2$, —CF$_3$, —C≡CR', —CH=CHR', —CH=CHCOR', —CHO, —C≡CR'', —CH=CHR'', —C≡C—CN, a five-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;

R' is H, C$_{1-6}$ alkyl, C$_{2-6}$ alkenyl, C$_{2-6}$ alkynyl, C$_{3-6}$ cycloalkyl; R'' is NO$_2$, NH$_2$, or N$_3$;

X is —O—, —NH— or —NCOR—; and

R is C$_{1-4}$ hydrocarbyl.

10. A method for preparing a compound according to claim 9, the reaction route being shown as follows:

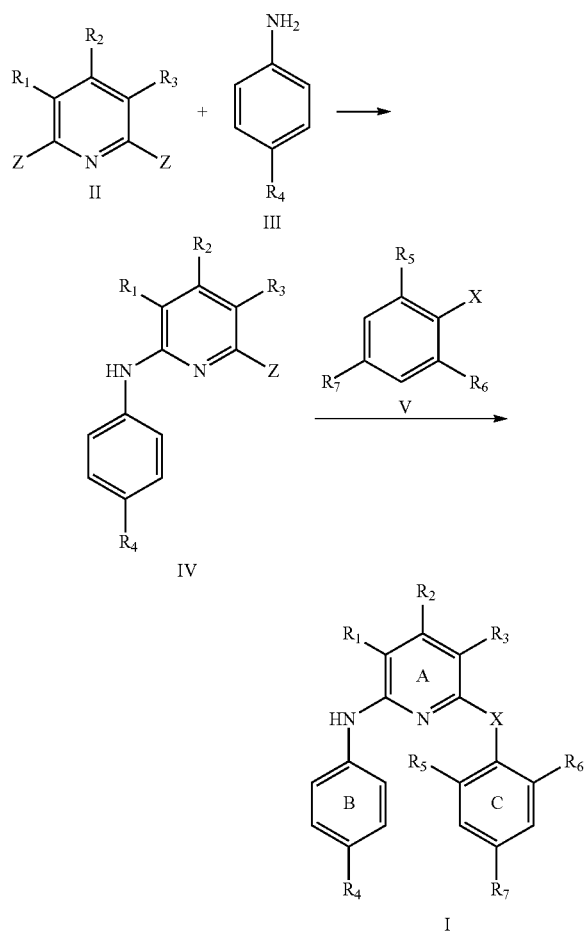

Z = Cl, Br, I
X = NH$_2$, OH, NHR, SH
X = NH, O, NR, S wherein $R_1$, $R_2$, $R_3$, $R_5$, $R_6$, $R_7$, and X are the same as defined for the compound of formula Ia in claim 7, $R_4$ is —CN; the method comprises reacting a substituted 2,6-dihalopyridine compound of formula II with a para-substituted phenylamine compound of formula III under the action of a base, or reacting in the absence of solvent, to form a 2-(4-substituted phenylamino) polysubstituted pyridine compound of formula IV; thereafter, coupling the intermediate of formula IV with a polysubstituted phenol or phenylamine compound of formula V, or heating in the presence of palladium catalysts or coupling under microwave condition, to form a 2-(4-substituted phenylamino) polysubstituted pyridine compound of formula I.

11. A pharmaceutical composition, comprising a compound or a pharmaceutically acceptable salt thereof of claim 9 and one or more pharmaceutically acceptable carriers or excipients.

12. A method of treating diseases or conditions associated with HIV infection, comprising administering to a subject in need thereof a therapeutically effective amount of a compound or a pharmaceutically acceptable salt thereof of claim 9.

13. A compound of formula I:

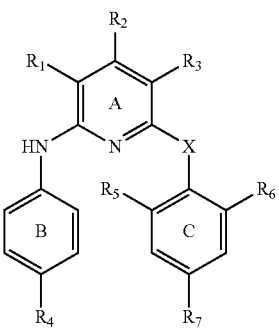

or a pharmaceutically acceptable salt thereof,
wherein $R_1$ and $R_3$ are each independently —H, halo, —NO$_2$, —NH$_2$, —NHR, —N(R)$_2$, —CN, —OH, C$_{1-6}$ alkyl, C$_{1-6}$ alkoxy, —CF$_3$, —SO$_3$H, —CONHR' or —COOR', $R_2$ is independently —H, halo, —NO$_2$, —NH$_2$, —NHR, —N(R)$_2$, —CN, —OH, C$_{1-6}$ alkoxy, —CF$_3$, —SO$_3$H, —CONHR' or —COOR', or $R_1$ and $R_2$ or $R_2$ and $R_3$ may together form —OCH$_2$O—;

$R_4$ is —CN, —CH=CH$_2$, —C≡CH, C$_{1-6}$ alkyl, C$_{1-6}$ alkoxy, —CF$_3$, halo, —NH$_2$, —OH, —COOH, —SO$_3$H, —C≡CR' or —CH=CHR';

$R_5$ and $R_6$ are each independently halo, C$_{1-6}$ alkyl, C$_{1-6}$ alkoxy, —CF$_3$, —NH$_2$, —OH, —SO$_3$H, —COOR', —NO$_2$, —CN, or —H;

$R_7$ is —CN, —HC=CH—CN, halo, C$_{1-6}$ alkyl, C$_{1-6}$ alkoxy, —NH$_2$, —CH$_2$—NHR', —OH, —NO$_2$, —CF$_3$, —C≡CR', —CH=CHR', —CH=CHCOR', CHO, —C≡CR'', —CH=CHR'', —C≡C—CN, a five- or six-membered heteroaryl containing 1-3 heteroatoms selected from the group consisting of N, O, S, and being optionally substituted on its ring with carbonyl (either aldehyde or ketone group), cyano, α,β-unsaturated cyano, alkenyl, alkynyl, aldehyde group or ketone group;

R' is H or C$_{1-6}$ hydrocarbyl; R'' is NO$_2$, NH$_2$, or N$_3$;

X is selected from the group consisting of —NH—, —O—, —S—, —CH$_2$—, —CO—, —CHOH—, —CHOR—, —NR—, —NCOR—; and R is C$_{1-4}$ hydrocarbyl, and wherein the compound is selected from the group consisting of:

2-(4-cyanophenylamino)-6-(2,6-dimethyl-4-bromophenoxy)-3-nitropyridine;

2-(4-cyanophenylamino)-6-(2,6-dimethyl-4-cyanophenoxy)-3-nitropyridine;

2-(4-cyanophenylamino)-6-(2,4,6-trimethylphenoxy)-3-nitropyridine;

2-(4-cyanophenylamino)-6-(2,6-dimethyl-4-formylphenoxy)-3-nitropyridine;

2-(4-cyanophenylamino)-6-(2,6-dimethyl-4-cyanovinylphenoxy)-3-nitropyridine;

3-amino-2-(4-cyanophenylamino)-6-(2,6-dimethyl-4-cyanophenoxy)-pyridine;

3-amino-2-(4-cyanophenylamino)-6-(2,6-dimethyl-4-hydroxymethylphenoxy)-pyridine;

2-(4-cyanophenylamino)-6-(2,6-dimethyl-4-hydroxymethylphenoxy)-3-nitropyridine;

2-(4-cyanophenylamino)-6-(2,6-dimethyl-4-allylphenoxy)-3-nitropyridine;

3-amino-2-(4-cyanophenylamino)-6-(2,6-dimethyl-4-cyanovinylphenoxy)-pyridine;

2-(4-cyanophenylamino)-6-(2,6-dimethyl-4-methylphenylamino)-3-nitropyridine;

3-amino-2-(4-cyanophenylamino)-6-(2,6-dimethyl-4-bromophenoxy)-pyridine;

3-amino-2-(4-cyanophenylamino)-6-(2,6-dimethyl-4-allylphenoxy)-pyridine;

2-(4-cyanophenylamino)-6-(2,6-dimethyl-4-(1-hydroxy-2-nitroethyl)phenoxy)-3-nitropyridine;

2-(4-cyanophenylamino)-6-(2,6-dimethyl-4-(2-cyclopropylaminomethyl) phenoxy)-3-nitropyridine;

2-(4-cyanophenylamino)-6-(2,6-dimethyl-4-iodophenoxy)-3-nitropyridine;

2-(4-cyanophenylamino)-6-(2,6-dimethyl-4-nitrophenoxy)-3-nitropyridine;

2-(4-cyanophenylamino)-6-(2,6-dimethyl-4-(3-methyl-3-hydroxy-1-butynyl)phenoxy)-3-nitropyridine;

3-amino-2-(4-cyanophenylamino)-6-(2,6-dimethyl-4-(3-methyl-3-hydroxy-1-butynyl)ethynylphenoxy)-pyridine;

2-(4-cyanophenylamino)-6-(2,6-dimethyl-4-(cyclopropylethynyl)phenoxy)-3-nitropyridine;

3-amino-2-(4-cyanophenylamino)-6-(2,6-dimethyl-4-(cyclopropylethynyl) phenoxy) pyridine;

2-(4-cyanophenylamino)-6-(2,6-dimethyl-4-ethynylphenoxy)-3-nitropyridine;

3-amino-2-(4-cyanophenylamino)-6-(2,6-dimethyl-4-ethynylphenoxy)-pyridine;

3-amino-2-(4-cyanophenylamino)-6-(2,6-dimethyl-4-aminophenoxy)-pyridine;

3-amino-2-(4-cyanophenylamino)-6-(2,6-dimethyl-4-iodophenoxy)-pyridine;

2-(4-cyanophenylamino)-6-(2,4,6-tribromophenoxy)-3-nitropyridine;

2-(4-cyanophenylamino)-6-(2,6-dibromo-4-formylphenoxy)-3-nitropyridine;

2-(4-cyanophenylamino)-6-(2,6-dibromo-4-hydroxymethylphenoxy)-3-nitropyridine;

2-(4-cyanophenylamino)-6-(2,6-difluorophenoxy)-3-nitropyridine; and 2-(4-cyanophenylamino)-6-(2,6-dibromo-4-cyanovinylphenoxy)-3-nitropyridine, or a pharmaceutically acceptable salt thereof.

14. A method for preparing a compound according to claim 13, the reaction route being shown as follows:

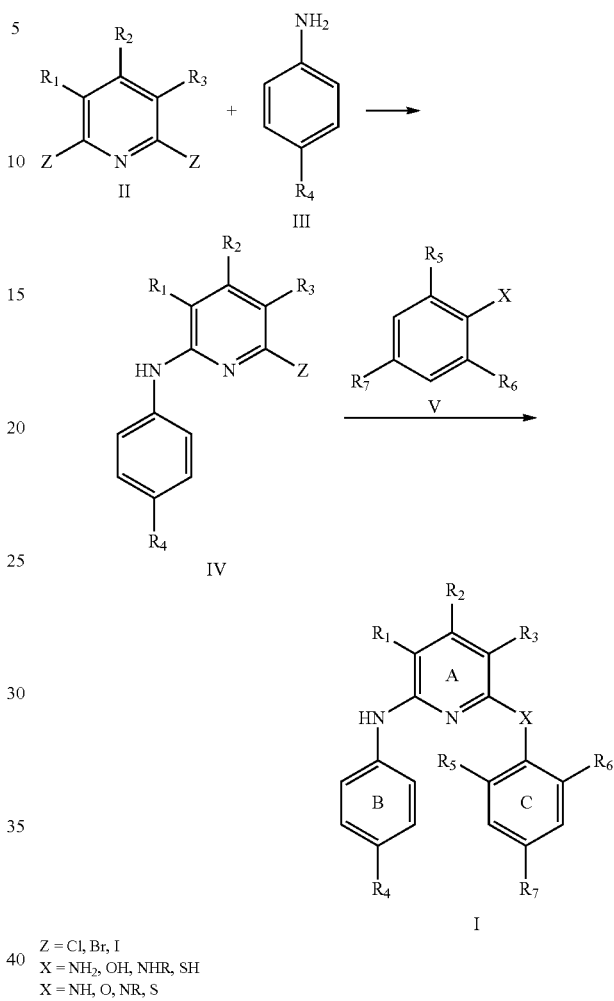

$Z = Cl, Br, I$
$X = NH_2, OH, NHR, SH$
$X = NH, O, NR, S$ wherein $R_1$, $R_2$, $R_3$, $R_4$, $R_5$, $R_6$, $R_7$, and X are the same as defined for the compound of formula Ia in claim 8; the method comprises reacting a substituted 2,6-dihalopyridine compound of formula II with a para-substituted phenylamine compound of formula III under the action of a base, or reacting in the absence of solvent, to form a 2-(4-substituted phenylamino) polysubstituted pyridine compound of formula IV; thereafter, coupling the intermediate of formula IV with a polysubstituted phenol or phenylamine compound of formula V, or heating in the presence of palladium catalysts or coupling under microwave condition, to form a 2-(4-substituted phenylamino) polysubstituted pyridine compound of formula I.

15. A pharmaceutical composition, comprising a compound or a pharmaceutically acceptable salt thereof of claim 13 and one or more pharmaceutically acceptable carriers or excipients.

16. A method of treating diseases or conditions associated with HIV infection, comprising administering to a subject in need thereof a therapeutically effective amount of a compound or a pharmaceutically acceptable salt thereof of claim 13.

* * * * *